United States Patent [19]
Crooks et al.

[11] Patent Number: 5,859,295
[45] Date of Patent: *Jan. 12, 1999

[54] CANAVANINE ANALOGS AND THEIR USE AS CHEMOTHERAPEUTIC AGENTS

[75] Inventors: Peter A. Crooks; Gerald A. Rosenthal, both of Lexington, Ky.

[73] Assignee: University of Kentucky Research Foundation, Lexington, Ky.

[ * ] Notice: This patent issued on a continued prosecution application filed under 37 CFR 1.53(d), and is subject to the twenty year patent term provisions of 35 U.S.C. 154(a)(2).

[21] Appl. No.: 665,827

[22] Filed: Jun. 18, 1996

Related U.S. Application Data

[63] Continuation-in-part of Ser. No. 353,270, Dec. 5, 1994, Pat. No. 5,552,440.

[51] Int. Cl.$^6$ .......................... C07C 59/48; C07C 229/00; C07D 205/00; A61K 31/44
[52] U.S. Cl. .......................... 562/553; 562/400; 562/405; 562/459; 562/465; 562/470; 562/561; 562/512; 562/899; 560/8; 560/19; 560/37; 560/42; 560/129; 560/155; 560/156; 560/160; 546/344; 548/950; 514/210; 514/345; 514/785; 514/784
[58] Field of Search .................................... 514/345, 553, 514/785, 50, 784; 562/465, 470, 899, 553; 560/37, 42, 156, 160; 548/950; 546/344

[56] References Cited

U.S. PATENT DOCUMENTS

| | | | |
|---|---|---|---|
| 2,792,398 | 5/1957 | Kyrides | 260/268 |
| 2,819,273 | 1/1958 | Drain et al. | 260/294.3 |
| 3,772,298 | 11/1973 | Bartman et al. | 260/268 R |
| 3,852,455 | 12/1974 | Carr | 424/267 |
| 3,988,456 | 10/1976 | Nishimura et al. | 424/250 |
| 4,066,070 | 1/1978 | Sukai et al. | 542/470 |
| 4,251,655 | 2/1981 | Scott et al. | 542/415 |
| 4,525,358 | 6/1985 | Baltes et al. | 514/255 |
| 4,757,074 | 7/1988 | Coker et al. | 514/255 |
| 4,895,841 | 1/1990 | Sugimoto et al. | 514/212 |
| 5,100,901 | 3/1992 | Sugimoto et al. | 514/319 |
| 5,318,967 | 6/1994 | Bruderer et al. | 514/232.8 |
| 5,552,440 | 9/1996 | Crooks et al. | 514/553 |

FOREIGN PATENT DOCUMENTS

| | | | |
|---|---|---|---|
| 0 229 391 | 7/1987 | European Pat. Off. | C07D 211/26 |
| 284359 | 9/1988 | European Pat. Off. . | |
| 0 296 560 | 12/1988 | European Pat. Off. | C07D 211/26 |
| 346791 | 12/1989 | European Pat. Off. . | |
| 585500 | 3/1994 | European Pat. Off. . | |
| 711763 | 5/1996 | European Pat. Off. . | |
| 4-202185 | 7/1992 | Japan | C07D 241/04 |
| WO 91/10650 | 7/1991 | WIPO | C07D 211/22 |
| WO 91/10651 | 7/1991 | WIPO | C07D 211/22 |
| WO 93/00906 | 1/1993 | WIPO . | |
| WO 93/13083 | 7/1993 | WIPO . | |

OTHER PUBLICATIONS

Rosenthal et al. J. Agri. Food Chem. (1991), 39, 987–990.
Rosenthal et al. J. Agri. Food Chem. (1995), 43, 2728–2734.
Rosenthal et al. J. Agri. Food Chem. (1988), 36, 1159–1163.
Rosenthal et al. J. Agri. Food Chem. (1989), 37, 591–595.
Ozinskas et al. BioOrganic Chemistry, (1986), 14, 157–162.
Chemical Abstracts, 70, 21 (1969), abstract 96754t.
Dankwardt et al, Tet. Let., 36, 28 (1995), pp. 4923–4926.
Protiva et al, Collect. Czech. Chem. Commun., 40, 12 (1975), pp. 3904–3923.
Chemical Abstracts, 53, abstract 20096f.
Chemical Abstracts, 53, abstracts 12306f and 12307d.
Chemical Abstracts, 53, abstract 9254b.
Chemical Abstracts, 53, abstract 8172b.

(List continued on next page.)

Primary Examiner—Jose G. Dees
Assistant Examiner—Sabiha N. Qazi
Attorney, Agent, or Firm—McDermott, Will & Emery

[57] ABSTRACT

This invention relates to canvanine analogs, their pharmaceutical compositions, and a method for treatment of cancer, particularly pancreatic cancer.

14 Claims, 4 Drawing Sheets

OTHER PUBLICATIONS

Baumgold, et al., European Journal of Pharmacology 251 (1994) 315–317.

Melchiorre, et al., J. Med. Chem, 1991, 36, 3734–3737.

Doods et al., Life Sciences, vol. 52, pp. 497–503 (1993).

Eberlein, et al., Trends in Pharmacol Sci Dec. 1989 pp. 50–54.

Logemann, et al., Brit. J. Pharmacol (1961) 17, 286–296.

Wilkerson et al, *J. Med. Chem.*, 36 (20)(1993), pp. 2899–2907.

Vidaluc et al, *J. Med. Chem.*, 37 (5) (1994), pp. 689–695.

Drukarch et al, *Eur. J. Pharmacol.*, 141 (1–2) (1987), pp. 153–157.

Provan et al, *Brit. J. Pharmacol.*, 111 (4) (1994), pp. 1103–1110.

Cheng et al, *Biochem. Pharmacol.*, 22 (1973), pp. 3099–3108.

Watson et al, *J. Pharmacol. Exp. Ther.*, 237 (1986), pp. 411–418.

Wynder EL, Cancer Res 35:2228, 1975.

Kissane, JM, J Surg Oncol 7:167, 1975.

MacMahon B. Cancer 50:676, 1982.

Hermanek P. Eur J Surg Oncol 17:167, 1991.

Moossa A.R. Cancer 50:2689, 1982.

Appelquist P et al. J. Surg Oncol 23:143, 1983.

Singh SM et al. Ann Surg 212: 132, 1990.

McGrath PC et al. Ann Surg 209 21, 1984. pp. 200–204.

Tepper J et al. Cancer 37: 1519, 1976.

Evans RM et al., Cancer 41:3288–3295,, 1981.

Tepper J et al.. IJ Radiat Oncol Biol Phys 12:9, 1986, (pp. 1687–1694).

Abe M & Takahashi M. Int J. Radiat Oncol Biol Phys 7 863, 1981.

Moertel CG et al. Surg 85:509, 1979.

Crown J et al. J Clin Oncol 9:1682, 1991.

Ardalan B & Singh G, J Clin Oncol 6:1053, 1988.

Rosenthal, GA, Q Rev Biol 52:155, 1997.

Rosenthal, GA, In: *Insecticides: Mechanism of Action and Resistance* D. Otto & B. Weber, eds, Intercept Ltd. Andover, England 1982. pp. 35–44.

Rosenthal GA, In: *Frontiers and New Horizons in Amino Acid Research,* K. Takai, ed. Elsevier, New York, 1992, pp. 108–118.

Rosenthal GA, Phytochemistry 30:1055, 1991.

Rosenthal, GA et al. J. Biol Chem 264:13693, 1989.

Rosenthal, GA et al. J. Biol Chem 264:9768, 1989.

Thomas DA & Rosenthal GA, Toxicol & Appl Pharm 91:405, 1987.

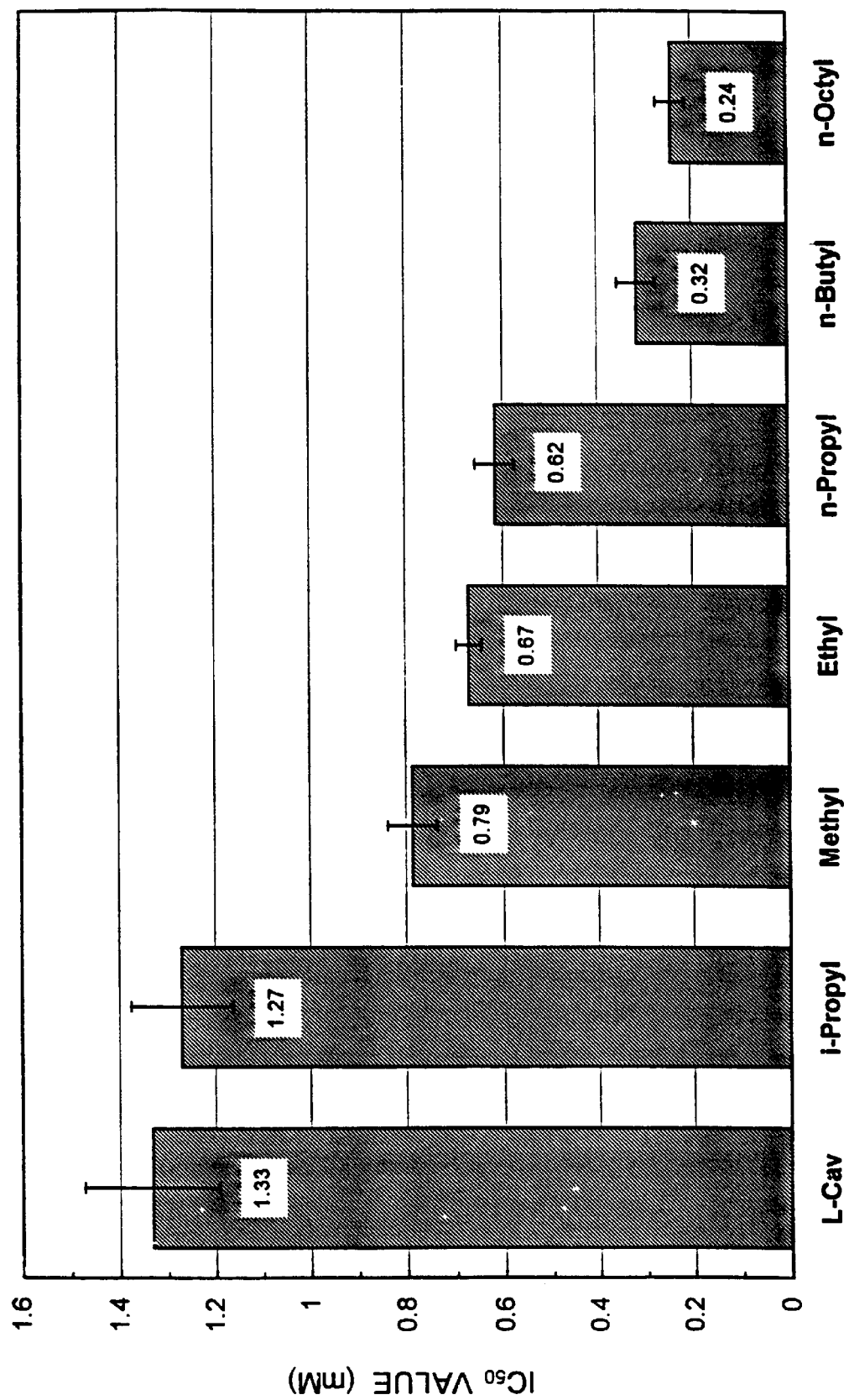

CANAVANINE ANALOGS AND THEIR USE AS CHEMOTHERAPEUTIC AGENTS

CROSS-REFERENCE TO RELATED APPLICATIONS

This application is a continuation-in-part of application Ser. No. 08/353,270, filed Dec. 5, 1994 now U.S. Pat. No. 5,552,440 which issued incorporated herein by reference in its entirety.

TECHNICAL FIELD

The invention relates to a pharmaceutical composition comprising canavanine analogs, and a method of treatment of cancer, particularly pancreatic cancer, with canavanine analogs.

BACKGROUND

L-Canavanine [L-2-amino-4-(guanidinooxy)butyric acid], a nonprotein amino acid found in certain leguminous plants[37], is a structural analog of L-arginine in which the terminal methylene group is replaced by oxygen. L-Canavanine, a substrate for arginyl-tRNA-synthetase, is incorporated into newly synthesized protein in place of arginine to create structurally aberrant and dysfunctional proteins[38]. Available evidence supports the contention that an important biochemical basis for canavanine's insecticidal and antitumor activities is the formation of dysfunctional canavanine-containing proteins.[39,40]

More than 26,000 people die each year in our country from pancreatic adenocarcinoma[1]. Death is the inevitable consequence to more than 90% of patients with this disease. It is the fourth most common cause of cancer death in men and the fifth most common for women[2]. Overall, it is the fourth most common carcinoma after those of the lung, colon and breast[3]. The incidence of this disease is linear with age to sixty but its occurrence increases markedly in the seventh or eighth decade of life[4]. There are several different histologies associated with cancer of the pancreas including small cell cancer, cystadenocarcinoma, islet cell tumors, lymphoma and carcinoid; however, 75–80% of the cases involve adenocarcinomas of ductal origin[5]. The only definitive risk factor in pancreatic cancer is cigarette smoking. A typical smoker accepts up to four times the risk of a nonsmoker[6].

Located in the upper abdomen in the retroperitoneum, the pancreas is associated intimately with many major structures including the portal vein, stomach, duodenum, common bile duct and the superior mesenteric artery. As the tumor grows, the patient's symptoms result from tumor infiltration of surrounding structure causing pain, nausea, vomiting, weight loss and jaundice. The latter condition presents symptoms in no more than one half of the patients. Once tumor infiltration occurs other structures such as the portal vein become affected and this precludes curative resectioning of the pancreas.

Effective treatment of pancreas cancer must achieve two difficult goals: control of the primary tumor mass, both initially and subsequently, and treatment of the metastatic tumor cells. As a result of its insidious onset, the diagnosis of pancreas cancer is delayed frequently for several months. This delay has profound implications, since metastatic spread to the liver or lymph nodes has been observed at a time of diagnosis in 60% of patients, and this factor diminishes the prospect for long-term survival[7]. Also, there are no known specific markers of carcinoma of the pancreas and it is asymptomatic in its early stage[8].

Conventional Therapy for Pancreatic Cancer

Currently, surgery is the primary and only curative therapy for pancreas cancer. However, only 15–25% of tumors are resectable at the time of diagnosis[9] and regrettably only 10–20% of patients resected will survive more than two years[10]. With these less than satisfactory surgical results, present day therapy has evolved in two directions: palliation of symptoms and aggressive multimodality treatment regimes which combine surgery with chemotherapy and radiation treatment.

Palliative therapy has become a major thrust of current treatment. Initial relief of symptoms has relied on surgery with surgical bypass of gastric outlet obstruction[11] and operative bypass of biliary obstruction[12]. Subsequent symptomatic treatment has centered around endoscopic placement of biliary stents to bypass tumors blocking the biliary tract[13] and/or percutaneous placement of bypass conduits[14].

Aggressive multimodality therapy combining chemotherapy and radiation therapy with surgery has been the response of choice when surgery alone was not effective. Radiation has been the cornerstone of therapy for unresectable cancer of the pancreas and 5-fluorouracil (5-FU) chemotherapy has been an important adduct to radiation treatment in these patients[15]. However, despite these valiant efforts, no patient survives five years.

A single, small randomized trial showed significant benefit from combined radiation and chemotherapy given two years after operation[16]. While this study was limited by an inadequate number of patients, nonetheless there was benefit to patients receiving multi-modality treatment.

Effective radiotherapy needs to maximize exposure of the affected tissues while sparing normal surrounding tissues. Interstitial therapy, where needles containing a radioactive source are embedded in the tumor, has become a valuable new approach. In this way, large doses of radiation can be delivered locally while sparing the surrounding normal structures[17]. Intraoperative radiotherapy, where the beam is placed directly onto the tumor during surgery while normal structures are moved safely away from the beam, is another specialized radiation technique. Again, this achieves effective irradiation of the tumor while limiting exposure to surrounding structures. Despite the obvious advantage of approaches predicated upon local control of the irradiation, patient survival is not significantly improved[18,19].

The foundation of chemotherapy for carcinoma of the pancreas has employed 5-FU[20]. Here too, the prognosis is bleak; no better than 10–15% of patients treated with 5-FU will experience a significant reduction in tumor size; overall survival rates are not improved. The addition of other chemotherapeutic agents such as cis-platin or adriamycin has not dramatically improved disease management[20]). For this reason, attempts to augment the intrinsic activity of 5-FU have been undertaken. On one approach, 5-FU is converted to 4-fluorodeoxyuridine monophosphate (FdUMP) which binds covalently to thymidylate synthase (EC 2.1.1.45). This competitive inhibitor disrupts DNA replication by curtailing deoxyuridine monophosphate anabolism to deoxythymidine.

Reduced folates such as leucovorin are a necessary cofactor for FdUMP binding to thymidylate synthase[21]. Cancer cells depauperate in reduced folate are resistant to 5-FU chemotherapy, but that resistance can be circumvented by providing exogenous reduced folate[22]. While 5-FU plus leucovorin relative to 5-FU alone has proven efficacious in treating colon cancer, patients with pancreas cancer received no benefit by receiving these two drugs in combination[23].

5-Fluorouracil can also be converted to 5-fluorouridine monophosphate which can be incorporated into mRNA thereby affecting protein translation. N-N- (phosphonacetyl) -L-aspartic acid (PALA) inhibits the transformation of aspartic acid to orotidine monophosphate which is converted subsequently to uridine monophosphate. The use of PALA provides a means of depleting essential uridine monophosphate. In the absence of uridine monophosphate, fluorouridine monophosphate is incorporated preferentially into mRNA which promotes cell death. Preliminary data from experiments employing high dose (2,600 mg/m$^2$) 5-FU after pretreatment with PALA have been promising, as significant tumor reduction has been noted in 5 of 6 patients[24]. However, subsequent phase II data have been less positive[25] with only one patient in 29 achieving any benefit. While new experimental efforts in treating pancreas cancer have been initiated, their limited success emphasizes the need for radically new approaches in the management of this devastating disease. The present invention provides an additional alternative for the treatment of cancers, particularly pancreatic cancer, by providing for a pharmaceutical composition comprising canavanine, and a method of treatment of cancer, particularly pancreatic cancer with canavanine.

DISCLOSURE OF THE INVENTION

The present invention provides a method of treating pancreatic cancer by administering a pharmaceutically effective amount of a composition comprising canavanine analogs to a patient with pancreatic cancer.

The canavanine analog compound may have a formula selected from:

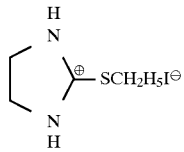

Formula 1

$R_1$ is selected from $SCH_2H_5I^{\ominus}$;

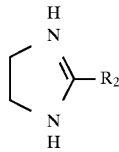

Formula 2

$R_2 = SC_2H_5$
$OC_2H_5$;

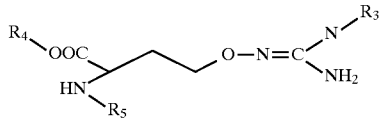

Formula 3 wherein $R_3$ is $H_2$; —$(CH_3)_2$; or H-Boc
$R_4$ is —$CH_2CH_3$; or —$CH_3$
$R_5$ is H; H-Boc; or

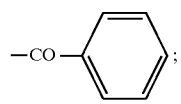

and

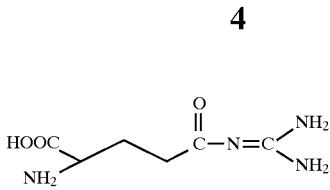

Formula 4

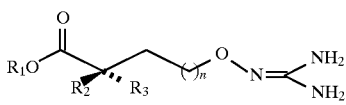

Formula 5

1 $R_1$=H, $R_2$=H, $R_3$=NH$_2$, n=1
2 $R_1$=H, $R_2$=H, $R_3$=NH$_2$, n=2
3 $R_1$=H, $R_2$=NH$_2$ $R_3$=H, n=1
4 $R_1$=H, $R_2$=NH$_2$ $R_3$=H, n=0
10 $R_1$=methyl, $R_2$=H, $R_3$=NH$_2$, n=1
11 $R_1$=ethyl, $R_2$=H, $R_3$=NH$_2$, n=1
12 $R_1$=isopropyl, $R_2$=H, $R_3$=NH$_2$, n=1
13 $R_1$=n-propyl, $R_2$=H, $R_3$=NH$_2$, n=1
14 $R_1$=n-butyl, $R_2$=H, $R_3$=NH$_2$, n=1
15 $R_1$=n-octyl, $R_2$=H, $R_3$=NH$_2$, n=1; and

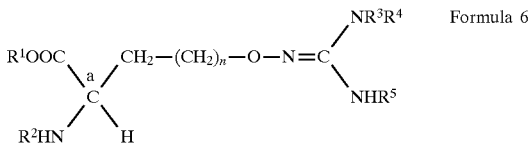

Formula 6

(a) $R^1$–$R^5$=H; n=0; a=S configuration
(b) $R^1$–$R^5$=H; n=1; a=S configuration
(c) $R^1$–$R^5$=H; n=1; a=R configuration
(d) $R^1$–$R^5$=H; n=2; a=S configuration
(e) $R^1$=CH$_3$; $R^2$–$R^5$=H; n=1; a=S configuration
(f) $R^1$=CH$_2$CH$_3$; $R^2$–$R^5$=H; n=1; a=S configuration
(g) $R^1$=CH$_2$CH$_2$CH$_3$; $R^2$–$R^5$=H; n=1; a=S configuration
(h) $R^1$=CH(CH$_3$)$_2$; $R^2$–$R^5$=H; n=1; a=S configuration
(i) $R^1$=(CH$_2$)$_3$CH$_3$; $R^2$–$R^5$=H; n=1; a=S configuration
(j) $R^1$=(CH$_2$)$_7$CH$_3$; $R^2$–$R^5$=H; n=1; a=S configuration
(k) $R^1$–$R^3$ =H; $R^4$, $R^5$=—CH$_2$ CH$_2$—, n=1; a=S configuration
(l) $R^1$=$R^2$=$R^5$=H; $R^3$=$R^4$=CH$_3$; n=1; a=S configuration
(m) $R^1$=$R^3$=$R^4$=$R^5$=H; $R^2$=C$_6$H$_5$CO; n=1; a=S configuration
(n) $R^1$=CH$_2$ CH$_3$; $R^2$=C$_6$H$_5$CO; $R^3$–$R^5$=H; n=1; a=S configuration.

The invention also provides a pharmaceutical composition comprising a pharmaceutically effective amount of a composition comprising canavanine analogs.

In an alternative embodiment the invention provides a pharmaceutical composition comprising a canavanine analog and 5-fluorouracil.

In still another embodiment, the invention provides a pharmaceutical composition comprising canavanine and a compound selected from the group consisting of (S)-2-aminoethyl-L-cysteine, L-2-azetidine carboxylic acid, L-selenomethionine, L-3-[N-hydroxy-4-oxypyridyl]-2-aminopropionic acid and mixtures thereof.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized, the invention is capable of modifications within the skill of the relevant art without departing from the spirit and scope of the invention.

BRIEF DESCRIPTION OF DRAWINGS

FIG. 4. Comparison of $IC_{50}$ values of L-canavanine and some of its esters.

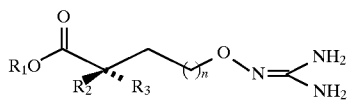

Figure 1:
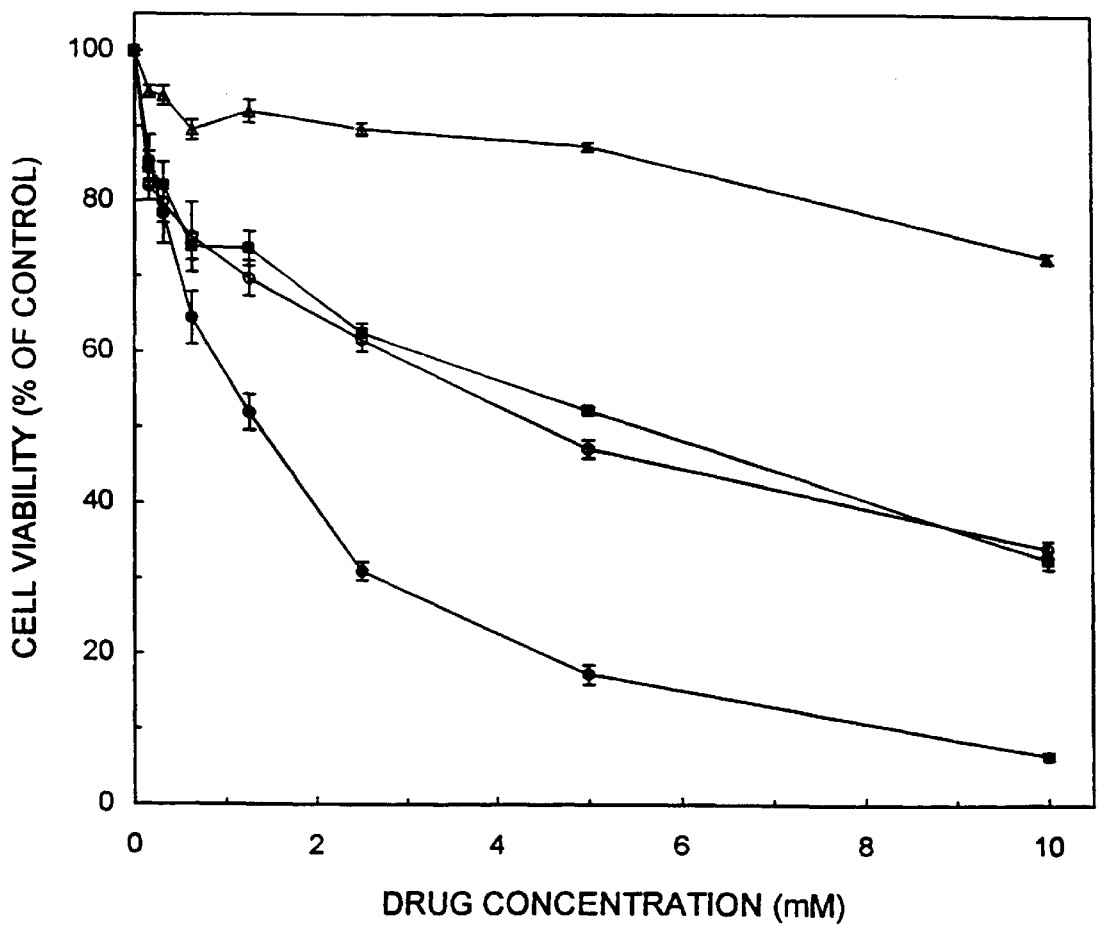
FIG. 1. The effect of canavanine enantiomers and chain length modifications on MIA-PaCa-2 cell viability. MIA-PaCa-2 cells were treated with the indicated concentration of: L-Canavanine (1, ●-), L-Homocanavanine (2, ■-), D-Canavanine (3, ⊖-), or D-2-Amino-3-(guanidinooxy) propionic acid (4, ▲-) See text for additional experimental details.

1 $R_1$=H, $R_2$=H, $R_3$=$NH_2$, n=1
2 $R_1$=H, $R_2$=H, $R_3$=$NH_2$, n=2
3 $R_1$=H, $R_2$=$NH_2$ $R_3$=H, n=1
4 $R_1$=H, $R_2$=$NH_2$ $R_3$=H, n=0
10 $R_1$=methyl, $R_2$=H, $R_3$=$NH_2$, n=1
11 $R_1$=ethyl, $R_2$=H, $R_3$=$NH_2$, n=1
12 $R_1$=isopropyl, $R_2$=H, $R_3$=$NH_2$, n=1
13 $R_1$=n-propyl, $R_2$=H, $R_3$=$NH_2$, n=1
14 $R_1$=n-butyl, $R_2$=H, $R_3$=$NH_2$, n=1
15 $R_1$=n-octyl, $R_2$=H, $R_3$=$NH_2$, n=1

DESCRIPTION OF THE INVENTION

The invention provides a pharmaceutical composition comprising a canavanine analog, and a method of treatment of cancer, particularly pancreatic cancer, with canavanine. A depiction of the basic canavanine molecule appears below.

In addition to the amino acids which are the building blocks of proteins, living systems also produce about 750 nonprotein amino acids[26]. These compounds possess a rich structural diversity and often elicit deleterious biological effects in viruses and all living systems[27], L-Canavanine, the L-2-amino-4-(guanidinooxy) butyric acid structural analog of L-arginine, is such a higher plant toxicant. Produced and stored by leguminous plants, canavanine is part of their chemical defense, where it functions as a barrier against a wide array of insects and other pests[28,29].

Biochemical Basis for Canavanine's Antimetabolic Properties

Studies with larvae of the tobacco horn worm, Manduca sexta, reveal that canavanine is an effective substrate for arginyl-tRNA synthetase. This canavanine-sensitive insect replaces on average at least one of three arginyl residues with canavanine in the de novo synthesized proteins of the hemolymph and body wall[30].

Vitellin, an essential egg protein, is constructed by the gravid migratory locust, Locusta migratoria migratorioides [Orthoplera] from amino acids released by degradation of vitellogenin⁻. Administration of canavanine to the female locust produces a canavanyl vitellogenin in which 18 of the nearly 200 arginine residues are replaced by canavanine[31]; thus, canavanine occurs about once every 225 amino acids. In spite of this paucity in canavanine content, it elicits a profound alteration in vitellogenin structure best observed by electrophoretic analysis.

Other chemical, physical, biochemical, and immunological tests confirm the dramatic change in the three dimensional conformation resulting from canavanine assimilation into this protein[31].

In response to microbial infection or mechanical injury, larvae of the meat-eating fly, Phormia terranovae, generate a group of antibacterial proteins known trivially as the diptericins. If canavanine is included at the time of mechanical injury, it is incorporated into newly produced diptericins[32]. Analysis of the diptericin activity of arginine- or canavanine-treated larvae reveals a nearly total loss of detectable biological activity for 3 of the 4 protective proteins-only diptericin A displays biological activity. Thus, canavanine incorporation into these protective proteins in place of arginine severely curtails their biological activity.

Manduca sexta larvae respond to injected fragments of the cell wall of Micrococcus lutea by producing lysozyme (EC 3.2.1.17), a protein which cleaves the mucopolysaccharide framework of the cell wall. Administration of 1 mg canavanine g⁻¹ fresh larval weight at the time of bacterial challenge generates canavanyl lysozyme with a ratio of canavanine to arginine of 1:3.8±0.2 (33). Canavanyl lysozyme exhibits a 50% loss of catalytic activity[33]. These insectan studies support the contention that the antimetabolic effects of canavanine reflect its incorporation into newly synthesized proteins which alter essential conformation and produces dysfunctional proteins.

Canavanine may be produced by isolating the amino acid from jack beans by the method of Kitagawa, Tokiyama, J. Biochem., (Tokyo) 11, 265 (1929) incorporated herein by reference in its entirety. See also Nyberg et al., J. Am. Chem. Soc., 79, 1222 (1957); Frankel et al., J. Am Chem. Soc., 3127 (1963); and Yamada et al., Agr., Biol. Chem., 37, 2201 (1973) for additional methods of synthesis of canavanine, also incorporated herein by reference.

Evaluation of Canavanine's Antineoplastic Activity

Canavanine's ability to disrupt the growth of rapidly dividing and growing larval cells led to whole animal studies of its antineoplastic activity. The inventors found that canavanine may be incorporated into key protein(s) unique to the cancer cell and that these structurally aberrant proteins, critical to the growth and proliferation of the cancer cell, may be dysfunctional.

EXAMPLE 1

Employing a solid rat colonic carcinoma in Fischer F433 rats, it was demonstrated that canavanine analogs of the invention possesses appreciable antineoplastic activity. For example, administration of a canavanine analog at a 3.0 g/kg dosing regimen for 5 consecutive days results in a 22% loss in tumor volume, while 9 days of daily dosing elicits a 60% diminution of the tumor[34].

However, the canavanine analogs are cumulatively toxic and can result in a weight loss of 19% in animals dosed with 3.0 g/kg canavanine for 5 days[34]. Additional experimentation established unequivocally that the observed body weight loss is not responsible for the canavanine analog compounds antitumor effects[34]).

EXAMPLE 2

Initial experimental efforts have been extended to determine if canavanine analog efficacy as an anticancer agent is increased in combination with 5-fluorouracil (5-FU). Providing a canavanine analog at 1.0 g/kg or 2.0 g/kg daily for 5 consecutive days with 5-FU significantly increases the antitumor activity of either drug alone (see FIG. 4). Body weight loss experienced by canavanine-treated animals increases in those animals given both drugs. These studies evidence that combination therapy offers a viable means of improving canavanine analogs intrinsic efficacy.

In order to improve canavanine analogs potential as chemotherapeutic agents, a number of canavanine analogs were evaluated for enhanced antitumor efficacy and diminished growth-inhibiting activity.

Enzyme activity studies conducted, reveal a number of other nonprotein amino acids whose assimilation into proteins disrupts normal catalytic activity. Some natural products such a (S) -2-aminoethyl-L-cysteine, L-2-azetidine carboxylic acid, L-selenomethionine, and L-3-[N-hydroxy-4-oxypyridyl]-2-aminopropionic acid or mixtures thereof are not only very active but also interact with canavanine to significantly amplify canavanine-mediated disruption of protein function[35].

Thus, there are a number of nonprotein amino acids besides canavanine able to substitute for their protein amino acid counterpart to generate dysfunctional proteins. These natural products often possess significant antitumor potential alone, in combination with canavanine, and with other therapeutic drugs.

The ability to assault the local cancer cell and even its metastatic offspring simultaneously with an array of nonprotein amino acid derivatives offers a weapon of considerable potential value.

Canavanine's Efficacy against Pancreatic Tumor

Analysis of L-[guanidinoxy-$^{14}$C] canavanine and other canavanine analog uptake into the protein of the major organs of the rat disclosed the highest radiolabeling in pancreatic proteins[36]. These proteins had 10 times the amount found in liver, muscle or brain samples. The efficient incorporation of radiolabeled canavanine into pancreatic proteins coupled with its demonstrated ability to create dysfunctional proteins prompted evaluation not only of canavanine but more importantly its derivatives as chemotherapeutic agents for human pancreas cancer.

A basic understanding of the biochemical basis for canavanine's antimetabolic properties has emerged over the past five years and these efforts have permitted development of a sound rationale for derivative synthesis. Chemical synthetic efforts, detailed herein, hold the promise of providing drugs with markedly enhanced efficacy and permit their administration at significantly lower dose levels than those required by canavanine. It has been unequivocally established that a 1 g $kg^{-1}$ dose of canavanine has no adverse effect on body weight nor on other discernible parameters of the rat.

A chemotherapeutic strategy predicated upon controlling cancer cell growth through the formation of structurally aberrant, dysfunctional proteins has been developed. Such macromolecules deny the cancer cell essential metabolites, undermine regulatory and other cellular control elements and pervasively disrupt critical cellular growth-related processes. Current treatment practices have not enjoyed substantial success and a radical new approach is justified. The approach of the invention is one with a strong biochemical foundation that provides a sound rationale for the development of new derivatives for use as chemotherapeutic agents. Most importantly, the canavanine analogs' mode of action is not directed at DNA replication, events that occur prior to transcription of the message, nor at message translation.

The present strategy for developing an effective chemotherapeutic agent does not focus on nucleic acid metabolism but rather at the level of protein function.

Evaluation of Drug Efficacy

A number of cell lines derived from pancreatic ductal adenocarcinoma have been established, including CFPAC-1 (ATCC CRL 1918), PANC-1 (ATCC CRL 1469), MIA-PaCa-1, and MIA-PaCa-2 (ATCC CRL 1420). MIA-PaCa2 is highly tumorigenic, has lost the ability to be growth regulated, and is derived from metastatic cells. CFPAC-1, which is derived from a primary tumor line, is the faster growing cell line and is preferable for whole animal studies. The availability of each of these lines from the American Type Culture Collection, 12301 Parklawn Drive, Rockville, Md., USA, insures an effective means for initial screening of newly synthesized derivatives both alone and in combination with other developed compounds as well as with drugs employed presently in human chemotherapy. The most promising candidates are employed in whole animal evaluation involving nude mice.

This invention permits an effective transition from laboratory findings and evaluations to their beneficial employment in alleviating the human suffering associated with this dreadful disease.

EXAMPLE 3

Antitumor Effect of Canavanine analogs in the Male Fischer Rat

The marked antitumor effect of canavanine analogs was demonstrated initially by our research group in studies on a solid, colonic carcinoma in male Fischer 344 rats. Administration of 3 g/kg canavanine analogs reproducibly prevented tumor growth during 5 or 9 consecutive treatment days. In fact, the final fresh tumor weight was typically 10% less than the weight of the initial tumor[34].

To enhance canavanine's antineoplastic activity, it was tested in combination with 5-FU. Providing canavanine at 1.0 g/kg or 2.0 g/kg daily for 5 consecutive days with 5-FU significantly increased the antitumor activity of either drug alone. This whole animal study was of considerable importance because it demonstrated that combination therapy offers a viable mean of improving canavanine's intrinsic efficacy and supports the contention that canavanine and its derivatives in conjunction with 5-FU may offer an effective chemotherapeutic strategy. Alternatively, canavanine therapy may be combined with radiotherapy.

EXAMPLE 4

The Effect of Canavanine on MIA-PaCa-I Cells

Work has been performed to evaluate the effect of canavanine on MIA-PaCa-1 cells. Cell survival was determined by the ability of viable cells grown on Dulbecco's modified medium to reduce tetrazolium dye to a colored formazan product. The experiment depicted in FIG. 4 dramatically discloses the potent efficacy of canavanine against these cells.

That the antitumor potential of canavanine analogs is related directly to the competing arginine concentration. This finding is of great importance because it reveals that canavanine is functioning as an effective arginine antagonist. This point is seminal to our contention that the antitumor effect of canavanine is related to its competition with arginine for arginyl-tRNA synthetase.

EXAMPLE 5
The Antineoplastic Effect of Canavanine in the Nude Mouse

Experiments with athymic nude mice were conducted with 6 treated and control mice. The palpable CFPAC-1-derived tumors grew slowly but after 28 days appreciable tumor growth had occurred in all experimental animals (FIG. 6A). By contrast, the CPFAC-1-derived tumors exhibited little growth in canavanine-treated animals (FIG. 6B). In 2 of the 7 experimental animals, a precipitous decline in tumor volume was observed during the first treatment week. These exciting experimental results add further support to the fact that canavanine and its derivatives possess considerable potential for the treatment of human pancreatic carcinoma.

A number of structural analogs of L-canavanine [L-2-amino-4-(guanidinooxy) butyric acid] the δ-oxa analog of L-arginine, have been synthesized and their growth-inhibitory effects evaluated in cultured MIA-PaCa-2 pancreatic carcinoma cells by the 3- (4.5-dimethylthiazol-2-yl) -2,5-diphenyltetrazolium bromide (MTT) assay. The results indicate that D-canavanine and analogs in which the carbon chain-length and/or terminal guanidinooxy functional group has been modified elicit less growth inhibitory activity than L-canavanine. On the other hand, several ester derivatives of L-canavanine have markedly enhanced growth inhibitory activity compared to L-canavanine. Thus, esterification constitutes an effective structural modification which significantly amplifies the growth inhibitory properties of the parent compound against MIA-PaCa-2 cells.

L-Canavanine at 3.0 g/kg daily dose for 5 days elicits significant inhibition of rat colon carcinoma, causing a 22% loss in tumor volume. A 60% loss in tumor volume is observed for a similar 9-day treatment period. However, during this treatment, L-canavanine exhibits significant cumulative toxicity in the form of weight loss of 19%[36,41]. Additional experiments have established that the reduction in tumor volume is not related to the observed body weight loss. Preliminary studies in nude mice carrying pancreatic ductal adenocarcinoma (CFPAC-1), show a significant decrease in final tumor volume after dosing animals with palpable tumors with 4 g/4 kg canavanine for 28 consecutive days. Canavanine proved even more effective when it was provided on a comparable dosing schedule which commenced 1 day after tumor cell implantation[42]. These studies reveal that canavanine is an effective chemotherapeutic agent for the treatment of pancreatic cancer.

On-going investigation of canavanine's antineoplastic activity demonstrates the value of developing canavanine analogs with diminished toxicity and enhanced potency. This application also describes synthetic methods for preparing a number of L-canavanine derivatives and evaluates their growth-inhibitory potency against cultured MIA-PaCa-2 cells.

Modifications of the canavanine molecule are based on the following considerations. First, since x-ray crystallographic studies have revealed that the interatomic distance between the β-carbon and the carbon of the guanidino group of canavanine is somewhat shorter than that in the arginine molecule[43], an insertion of an extra methylene group into the canavanine molecule while retaining the important guanidinooxy functional group was considered to be an effective alteration which might result in an increase in affinity for the arginyl-tRNA synthetase active site. Similarly, the chain-shortened analog, in which only one methylene group is present in the molecule was evaluated. Second, it is reasonable to contend that the antitumor activity of canavanine is stereospecific for the L-isomer, since arginyl-tRNA synthetase would undoubtedly recognize only the L-enantiomer of arginine as a substrate. Hence, the biological activity of the D-enantiomer of canavanine was pursued to determine if it exhibited MIA-PaCa-2 cell growth-inhibitory activity and to compare the activity of this stereoisomeric form with that of its naturally occurring antipode. It was believed that D-canavanine would not be an arginyl-tRNA synthetase substrate; thus, any adverse effects noted with D-canavanine could not result directly from its incorporation into newly synthesized protein. In this respect, the D-enantiomer offers a means of evaluating canavanine's activity divorced from its role in protein synthesis. Third, ionic and hydrogen-bonding interactions of the guanidino group of arginine with neighboring amino acid residues are crucial for establishing the three-dimensional structure of a protein; replacement of this moiety with the guanidinooxy moiety of canavanine results in the formation of aberrant and dysfunctional protein.[30,44] Thus, analogs in which the guanidinooxy group has been further modified appears to cause a greater deleterious effect on the tertiary/quatenary structure of arginyl-containing proteins than does canavanine. Thus, the effect of structural alteration of the terminal guanidinooxy group of L-canavanine was also evaluated.

Finally, the methyl, ethyl, isopropyl, n-propyl, n-butyl, and n-octyl esters of L-canavanine exhibit greater lipophilicity than canavanine and appear to possess improved cell membrane penetration properties. These compounds can constitute prodrug candidate forms of L-canavanine, and can be attacked by cytosolic esterases to generate the parent compound.

Chemistry

L-2-Amino-5-(guanidinooxy)pentanoic acid (L-HMCAV, homocanavanine; 2) and D-canavanine (D-CAV); 3) were synthesized from D-methionine and L-glutamic acid 5-methyl ester respectively, as reported in Rosenthal et al.[45]. The shortened chain-length analog of D-canavanine, D-2-amino-3-(guanidinooxy)propionic acid (D-GOA, 4) was synthesized via ring opening of D-cycloserine (5) to give D-2-amino-3-(aminooxy)propionic acid (6), followed by zinc-mediated guanidination with cyanamide (Scheme 1).

Structural alteration of the guanidinooxy group of canavanine, as in the ethylene (L-ETCAV, 8) or dimethyl analog (L-DMCAV, 9), was achieved by reacting the copper salt of L-canaline (7) with 2-ethoxyimidazoline or dimethylcyanamide, respectively (Scheme 2). L-Canavanine esters were produced by heating L-canavanine (L-CAV, 1) with the appropriate anhydrous alcohol saturated with HCl gas.

DETAILED DESCRIPTION OF THE FIGURES

As shown in FIG. 1, cell viability assays indicate that alteration of the number of methylene groups between the amino β-carbon and the guanidinooxy group does not enhance the growth-inhibitory effects of the parent compound in cultured MIA-PaCa-2 cells. Decreasing the number of methylene groups from 2 to 1, in addition to inverting the stereochemistry at C-2 (D-GOA, 4) results in almost complete loss of growth-inhibitory activity when compared to that of L-canavanine. An increase in methylene group number from two to three (L-homocanavanine, L-HMCAV, 2) affords a compound that exhibits only weak growth inhibitory properties. These results are consistent with the belief that chain shortening produces an analog less likely to be recognized as a substrate for arginyl-tRNA synthetase and would therefore not be efficiently incorporated into protein. The results obtained for the chain-lengthened analog suggest that a crucial intra-atomic distance is required between the amino acid functionality and the terminal guanidinooxy moiety for recognition by the amino acyl synthetase enzyme.

The D-isomer of canavanine (3) exhibits a weak but significant decrease in growth-inhibitory activity against MIA-PaCa-2 cells, and was similar in potency to the chain-elongated L-homocanavanine (2). Thus, the L-isomer of canavanine is significantly more effective in the growth inhibitory activity than the D-isomer, which may reflect the different abilities of these enantiomers to be incorporated into arginyl-containing protein. The growth inhibiting activity of D-canavanine also suggests that D-canavanine's antimetabolic properties result from factors other than aberrant, canavanyl protein formation.

Figure 2:
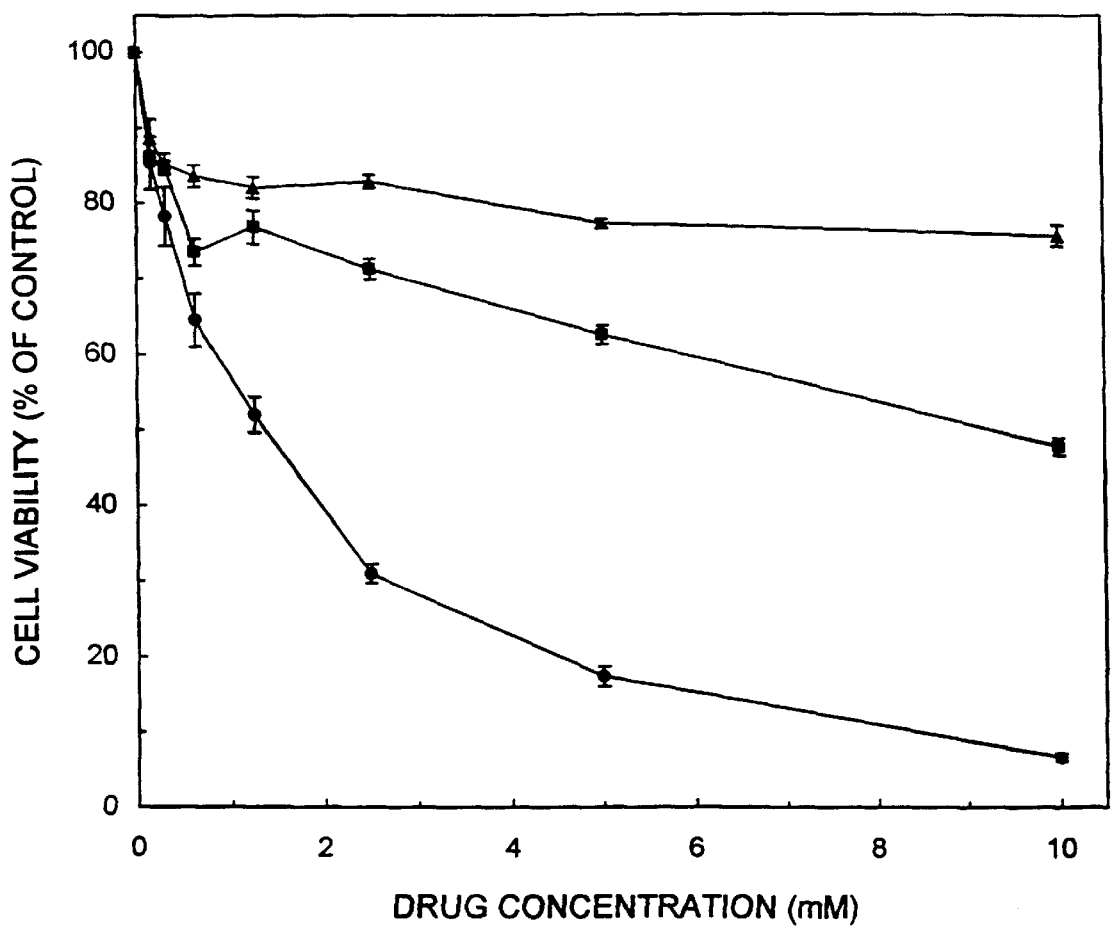
FIG. 2. The effect of structural modification of the guanidinooxy group of L-Canavanine on MIA-PaCa-2 cell viability. MIA-Pa-Ca cells were treated with the indicated concentration of: L-Canavanine (1, ●-), L-2-Amino-4-(1-imidazolideneaminooxy) butanoic acid (8, ■-), or L-2-amino-4-[assym-$N^G$, $N^G$-dimethyl(guanidinooxy)] butanoic acid (9, ▲-).

Structural modification of the guanidinooxy functional group (8 and 9) affords compounds with significantly reduced growth inhibitory activity against cultured MIA-PaCa-2 cells, as compared to L-canavanine (FIG. 2). The assym-$N^G$, $N^G$-dimethyl analog (9) exhibits weak growth-inhibitory properties and is slightly less active than the $N^G$, $N^G$-ethylene analog (9). The results suggest that an intact guanidinooxy group is required for maximum growth-inhibitory activity.

Figure 3:
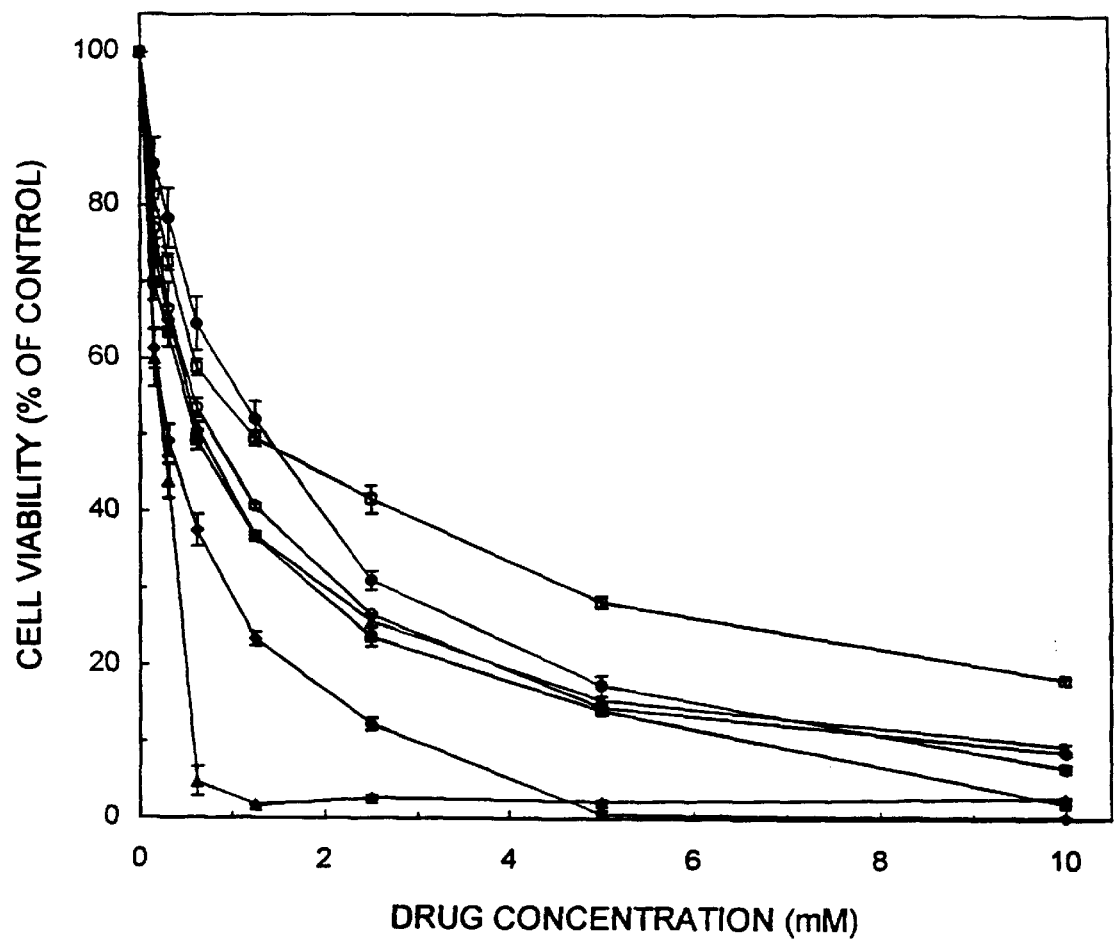
FIG. 3. The effect of L-canavanine esters on MIA-PaCa-2 cell viability. MIA-PaCa-2 cells were treated with the indicated concentration of: L-Canavanine (1, ●-), L-Canavanine Methyl Ester 2HCl (10, ▲-), L-Canavanine Ethyl Ester 2HCl (11, ⊖-), L-Canavanine Isopropyl Ester 2HCl (12, ⊞-), L-Canavanine n-Propyl Ester 2HCl (13, ■-), L-Canavanine n-Butyl Ester 2HCl (14, -♦), or L-Canavanaine n-Octyl Ester 2HCl (15, ▲-). See text for additional experimental details.

The methyl, ethyl, and n-propyl esters (10, 11, 13) of canavanine exhibit slightly improved growth-inhibitory activities in MIA-PaCa-2 cells with $IC_{50}$ values of 0.79, 0.67, and 0.62 mM, respectively, when compared to L-canavanine ($IC_{50}$ value=1.33 mM, FIG. 3 and 4). Interestingly, the n-butyl and n-octyl esters of L-canavanine (14, 15) elicit the most significant increase in growth inhibitory activity with $IC_{50}$ values of at 0.32 and 0.24 mM, respectively. This improved potency may be due to the increased lipophilicity and enhanced membrane-penetrational properties of the ester analogs.

When compared to L-canavanine, the isopropyl ester (12), whose $IC_{50}$ is 1.27 mM, also shows a slight increase in growth inhibitory activity up to a concentration of 1.5 mM; at higher concentrations, this ester was less active than L-canavanine. Compared to the other esters that were evaluated, the isopropyl ester is more sterically hindered around the carbonyl moiety of the ester functionality and therefore more resistant to enzymatic hydrolysis, this factor appears to account for its lower overall activity. Since zwitterion formation is not possible for esters of amino acids, these esters showed enhanced lipophilicity and better transport characteristics than the parent amino acid. This property may provide a basis for the development of effective prodrug analogs of L-canavanine that possess greater bioavailability.

EXAMPLE 6
Human Pancreatic Carcinoma Cell Culture and Cell Viability Assays

Human pancreatic carcinoma cells (MIA-PaCa-2) were purchased from the American Type Cell Collection (ATCC). The cells were grown in Dulbecco's Modified Eagle's Medium (DMEM) containing 10% (v/v) fetal calf serum.

Cell viability assays were performed with MIA-PaCa-2 cells in culture at the following drug concentrations: 0.16, 0.31, 0.62, 1.25, 2.5, 5.0, and 10.0 mM. The drugs were dissolved into and diluted with DMEM.

Cell viability was assessed by the metabolic 3-(4,5-dimethylthiazol-2-yl)-2,5-diphenyltetrazolium bromide (MTT) assay previously described by Kissane[5] with minor modifications. The metabolic MTT assay measured the ability of viable cells to reduce a tetrazolium dye to a formazan chromogen, which could be measured at 630 nm. MIA-PaCa-2 cells, maintained in exponential growth for up to 72 hr. were plated at $5 \times 10^3$ cells/well in a 96-well plate. The cells were allowed to grow for 24 h. prior to drug addition. Four replicate wells were used for the drug-free control and for each drug concentration. MTT assays were performed 48 h. after addition of the drug. Viability was calculated as the percentage of the drug-free control cell population ± SEM.

Silica gel plates (2.5×7.5 cm, 250 μm layer, fluorescent at 254 nm) were purchased from Diamond Whatman International, Ltd. (Clifton, N.J.). Column chromatographic separations were carried out with silica gel (200–400 mesh, 60 Å) from Fisher/Aldrich (Milwaukee, Wis.). Chemicals and solvents were secured from Fisher/Aldrich Chemical Co. Melting points were recorded on a Fisher-Johns melting point apparatus, and are uncorrected. $^1$H-NMR and $^{13}$C-NMR spectra were carried out on a Varian VXR-300 MHz spectrometer (Palo Alto, Calif.); spectra were run at 21° C. in either $CDCl_3$, $DMSO-d_6$, or $D_2O$ using tetraethyl silance (TMS) or the sodium salt of 3-(trimethyulsilyl) propionic-2,2,3,3-$d_4$ acid (TSP) as an internal standard. Elemental analyses were performed by Atlantic Microlabs (Norcross, Ga.), $[\alpha]_D^{23}$ values were observed at 589 nm and determined on a Perkin-Elmer 241 polarimeter. MS data were carried out on a Kratos concept 1H MS50 spectrometer.

EXAMPLE 7
D-2-Amino-3-(aminooxy)propionic acid dihydrochloride (6)

D-Cycloserine (5, 408 mg. 4 mmol) was dissolved in 2N HCl (20 mL); the resulting solution was kept at 60° C. for 6 h. After cooling to 0° C., the solution was adjusted to pH 4.5 with 15% (w/v) NaOH and was applied to a 25 cm$^3$ Dowex 50×8 (H$^+$) column. The resin was washed with deionized water (500 mL) followed by 5N $NH_4OH$ (80 mL). The column effluent was concentrated by rotary evaporation in vacuo to give 6 (480 mg, 99% yield) as a colorless solid, m.p. 167.0°–169.5° C.; $[\alpha]_D^{23}$=+24.5° (c=2.15, $H_2O$); $^1$H-NMR ($D_2O$); δ4.79 (dd, J=11.0, 5.2 Hz, 1H, 3-$CH_{2a}$) 4.62 (dd, J=11.0, 3.0 Hz, 1H, 3-$CH_{2b}$), 4.55 (dd, J=5.2, 3.0 Hz, 1H, 2-CH) ppm; $^{13}$C-NMR ($D_2O$): δ170.95 (C-1), 74.19 (C-3), 54.41 (C-2) ppm; Anal ($C_3H_{10}Cl_2N_2O_3$) C, H, N, Cl.

EXAMPLE 8
D-2-Amino-3 (guanidinooxy)propionic acid (4)

Copper oxide (750 mg) was added to a solution of 6 (480 mg, 4 mmol) in distilled water (5 mL). The mixture was heated for 5 min at 100° C., for 2 h. at 50° C., and for 24 h. at 23° C. The unreacted CuO was filtered, and the filtrate was adjusted to pH 9.2 with 1N NaOH. This solution was then added to a solution of cyanamide (190 mg, 4.60 mmol) and $ZnCl_2$ (705 mg, 5.2 mmol) dissolved in a minimum amount of water. The resulting mixture was stirred at 50° C. for 3 days. The reaction was terminated by bubbling hydrogen sulfide through the reaction mixture for 10 min; the resulting precipitate was filtered. The filtrate was evaporated to dryness by rotary evaporation in vacuo to give 300 mg of crude product (45% yield). Part of this product was then applied to a cellulose column (15×1 cm) and eluted with ethanol: 0.2N NH$_4$OH (70:30). The last eluting fraction was evaporated to dryness to give pure 4 as a glassy solid; [α]$_D^{23}$=+7.5° (c=1.35, H$_2$O); $^1$H-NMR (D$_2$O): δ4.28 (dd, J=6.0, 3.6 Hz, 1H, 2-CH), 4.14 (dd, J=11.0, 3.6 Hz, 1H, 3-CH$_{2a}$), 4.08 (dd, J=11.0, 6.0 Hz, 1H, 3-CH$_{2b}$) ppm; $^{13}$C-NMR (D$_2$O): δ177.14 (C-1), 159.42 (C=N) 75.63 (C-3), 58.91 (C-2) ppm.

EXAMPLE 9

L-2-Amino-4(1-imidazolideneaminooxy)butanoic acid (8)

The ethylene analog of canavanine 8, was obtained by treatment of the copper salt of L-canaline (1 mmol, 7), prepared as described for 4, with 2-ethoxyimidazoline (240 mg, 1.8 mmol) in water (5 mL) at 45° C. for 4 days. After adjusting the solution to pH 5.0 with 1N NaOH, hydrogen sulfide was bubbled through for 5 min. The acidic reaction mixture was filtered and the filtrate adjusted to pH 3.4 with 1N NaOH. This solution was applied to a 25 cm$^3$ column of Dowex 50×8 (NH$_4^+$) and the resin was washed with distilled water (500 mL) followed by 0.2N NH$_4$OH (400 mL). The ammonia wash was evaporated to dryness by rotary evaporation in vacuo, and the resulting residue was purified by cellulose column chromatography (25×1 cm) by elution with n-BuOH:AcOH:H$_2$O (4:1:1). Fractions containing 8 were combined and the solvent was removed by rotary evaporation in vacuo to give pure 8 (29 mg, 16%) as a glassy solid; [α]$_D^{23}$=+9.6° (c=2.4, H$_2$O); $^1$H-NMR (D$_2$O): δ4.08–4.17 (m, 2H, 4-CH$_2$), 3.90 (t, J=6.0 Hz, 1H, 2-CH), 3.80 (s, 4H, NCH$_2$CH$_2$N), 2.27 (dt, J=6.0 Hz, 2H, 3-CH$_2$) ppm; $^{13}$C-NMR (CDCl$_3$): δ176.66 (C-1), 164.09 (C=N), 75.72 (C-4), 54.99 (C-2), 45.75 (2×NCH$_2$), 31.51 (C-3) ppm; HRFABMS calcd. for C$_7$H$_{14}$N$_4$O$_3$ 203.1144 (MH+), found 203.1128.

EXAMPLE 10

L-2-Amino-4-[assym-N$^G$, N$^G$-dimethyl (guanidinooxy)] butanoic acid (9)

Compound 9 (71% yield) was obtained as a colorless solid utilizing the procedure described for the preparation of 8, but using dimethylcyanamide in place of 2-ethoxyimidazoline, m.p. 175.0°–177.0° (dec.); [α]$_D^{23}$=+4.6° (c=1.6, H$_2$O); $^1$H-NMR (D$_2$O): δ3.98 (t, J=6.0 Hz, 2H, 4-CH$_2$), 3.82 (t, J=6.0 Hz, 1H, 2-CH), 2.82 (s, 6H, 2×CH$_3$) ppm; $^{13}$C-NMR (D$_2$O): δ177.90 (C-1), 162.80 (C=N), 72.26 (C-4), 55.39 (C-2), 39.49 (2×CH$_3$), 32.73 (C-3) ppm; Anal. (C$_7$H$_{16}$N$_4$O$_3$.0.25H$_2$O) C,H,N.

EXAMPLE 11

L-Canavanine Esters

The methyl, ethyl, isopropyl and n-propyl esters of canavanine (10–13) were prepared by heating a solution of L-canavanine (1, 1 mmol) in the appropriate anhydrous alcohol (6 mL) saturated with dry HCl at 80° C. for 1 h. The reaction mixture was filtered and the filtrate removed by rotary evaporation in vacuo to give a clear, gummy residue. The residue was triturated with anhydrous ether (2 mL) and the solvent decanted off. The resulting solid was then dried under high vacuum (0.5 mm Hg). The n-butyl and n-octyl esters of canavanine (14,15) were similarly prepared with the following modifications: the heating time was increased to 3 h. in 17% HCl/anhydrous 1-butanol (w/w) and 24 h. in 11% HCl/anhydrous 1-octanol (w/w), respectively. The method for preparing the octyl ester of canavanine is described in detail in the experimental section.

EXAMPLE 12

Methyl L-2-amino-4-guanidinooxybutanoate (10)

Compound 10 was obtained as a white hygroscopic solid (71% yield); [α]$_D^{23}$=+19.5° (c=0.45, H$_2$O); $^1$H-NMR (DMSO-d$_6$): δ8.90 (br s, 3H, NH$_3^+$), 7.80 (s, 5H, C(N H$_2$)NH$_3^+$), 4.10 (br s, 1H, 2-CH), 3.80–4.00 (m, 2H, 4-CH$_2$), 3.70 (s, 3H, OCH$_3$), 2.00–2.30 (m, 2H, 3-CH$_2$) ppm; $^{13}$C-NMR (DMSO-d$_6$): δ169.29 (C-1), 158.39 (C=N), 71.87 (C-4), 52.90 (CH$_3$), 48.88 (C-2), 28.14 (C-3) ppm; Anal. (C$_6$H$_{16}$Cl$_2$N$_4$O$_3$.1 H$_2$O.0.1 CH$_3$OH) C, H, N, Cl.

EXAMPLE 13

Ethyl L-2-amino-4-guanidinooxybutanoate (11)

Compound 11 was obtained as a white hygroscopic solid (75% yield); [α]$_D^{23}$=+18.3° (c=0.52, H$_2$O); $^1$H-NMR (DMSO-d$_6$): δ9.00 (br s, 3H, NH$_3^+$), 7.83 (s, 5H, C(N H$_2$)NH$_3^+$), 4.18(q, J=6.5 Hz, 2H OCH$_2$CH$_3$), 4.10 (t, J=6.5 Hz, 1H, 2-CH), 3.85–4.00 (m, 2H, 4-CH$_2$), 2.10–2.30 (m, 2H, 3-CH$_2$) ppm; $^{13}$C-NMR (DMSO-d$_6$): δ169.12 (C-1), 158.63 (C=N), 72.11 (C-4), 62.00 (CH$_2$OOC), 49.17 (C-2), 28.42 (C-3), 13.99 (CH$_3$CH$_2$) ppm; Anal. (C$_7$H$_{18}$Cl$_2$N$_4$O$_3$.0.8 H$_2$O. 0.12 C$_2$H$_5$OH) C, H, N, Cl.

EXAMPLE 14

Isopropyl L-2-amino-4-guanidinooxybutanoate (12)

Compound 12 was secured as a white hygroscopic solid (54% yield); [α]$_D^{23}$=+16.1° (c=0.54, H$_2$O); $^1$H-NMR (DMSO-d$_6$): δ9.00 (br s, 3H, NH$_3^+$), 7.84 (s, 5H, C(N H$_2$)(NH$_3^+$), 4.98 (sept, J=6.5 Hz, 1H OCH), 4.06 (t, J=6.0 Hz, 2-CH), 3.90–4.00 (m, 2H, 4-CH$_2$), 2.10–2.25 (m, 2H, 3-CH$_2$), 1.22 (d, J=6.0 Hz, 6H, 2×CH$_3$) ppm; $^{13}$C-NMR (DMSO-d$_6$): δ168.58 (C-1), 158.59 (C=N), 72.03 (C-4), 69.90 (CH(CH$_3$)$_2$), 49.17 (C-2), 28.40 (C-3), 21.41, 21.32 (2×CH$_3$) ppm; Anal. (C$_8$H$_{20}$Cl$_2$N$_4$O$_3$.1.7 H$_2$O) C, H, N, Cl.

EXAMPLE 15 n-Propyl L-2-amino-4-guanidinooxybutanoate (13)

Compound 13 was obtained as a white hygroscopic solid (96%); [α]$_D^{23}$=+28.7° (c=0.48, H$_2$O); $^1$H-NMR (DMSO-d$_6$): δ8.20–9.20 (br s, 3H, NH$_3^+$), 7.80 (s, 5H, C(NH$_2$)N H$_3^+$), 4.08–4.22 (m, 2H, OCH$_2$) 3.94–4.04 (t, 1H, 2-CH), 3.81 (2H, 4CH$_2$), 2.08–2.32 (m, 2H, 3-CH$_2$), 1.58–1.72 (m, 2H, OCH$_2$CH$_2$), 0.88–0.96 (t, 3H, CH$_3$) ppm; $^{13}$C-NMR (DMSO-d$_6$): δ169.09 (C-1), 158.36 (C=N), 71.95 (C-4), 67.22 (CH$_2$O), 49.05 (C-2), 28.30 (C-3), 21.24 (CH$_2$CH$_2$O), 10.11 (CH$_3$) ppm; Anal. (C$_8$H$_{20}$Cl$_2$N$_4$O$_3$.1.1 H$_2$O.0.16 C$_3$H$_7$OH) C, H, N, Cl.

EXAMPLE 16 n-Butyl L-2-amino-4-guanidinooxybutanoate (14)

Compound 14 was obtained as a white hygroscopic solid (91% yield); [α]$_D^{23}$=+16.7° (c=0.88, H$_2$O); $^1$H-NMR (DMSO-d$_6$): δ8.20–9.20 (br s, 3H, NH$_3^+$), 7.80 (s, 5H, C(N H$_2$)NH$_3^+$), 4.18 (m,2H,(OCH$_2$), 4.00 (t, 1H, 2-CH), 3.35 (t,2H, 4-CH$_2$, overlap with water peak), 2.08–2.28 (m, 2H, 3-CH$_2$), 1.54–1.64 (m, 2H, OCH$_2$CH$_2$), 1.26–1.44 (m, 2H, OCH$_2$CH$_2$CH$_2$), 0.84–0.94 (t, 3H, CH$_3$) ppm; $^{13}$C-NMR (DMSO-d$_6$): δ169.08 (C-1), 158.32 (C=N), 71.91 (C-4), 65.46 (CH$_2$O), 49.06 (C-2), 29.84 (CH$_2$CH$_2$O), 28.29 (C-3), 18.35 (CH$_2$CH$_2$CH$_2$), 13.41 (CH$_3$) ppm; Anal. (C$_9$H$_{22}$Cl$_2$N$_4$O$_3$.0.75 H$_2$O. 0.25 C$_4$H$_9$OH) C, H, N, Cl.

EXAMPLE 17 n-Octyl L-2-amino-4-guanidinooxybutanoate (15)

L-canavanine (0.20 g, 1.13 mmol) was heated in 5 mL of 11% HCl/anhydrous octanol (w/w) at 80° C. for 24 h. The resulting mixture was filtered. The solvent was removed under high vacuum with gentle heating at 50°–60° C. The viscous residue was dissolved in 1 mL of water and the resulting solution was lyophilized. A clear hygroscopic (0.04 g) residue was obtained (10% yield); $[\alpha]_D^{23}=+7.6°$ (c=0.485, H$_2$O); $^1$H-NMR (DMSO-d$_6$): δ8.80–9.60 (br s, 3H, NH$_3^+$), 7.80 (s, 5H, C(NH$_2$)NH$_3^+$), 4.12–4.20 (t,2H, OCH$_2$), 3.92–4.00 (t, 1H, 2-CH), 3.35 (t, 2H, 4-CH$_2$, overlap with water peak), 2.04–2.24 (m, 2H, 3-CH$_2$), 1.56–1.66 (m, 2H, OCH$_2$CH$_2$), 1.22–1.38 (m, 10H, OCH$_2$CH$_2$(CH$_2$)$_5$), 0.82–0.90 (t, 3H, CH$_3$) ppm; $^{13}$C-NMR (DMSO-d$_6$): δ169.10 (C-1), 158.33 (C=N), 71.91 (C-4), 65.72 (CH$_2$O), 49.06 (C-2), 31.11, 28.47, 28.46, 28.31, 27.81, 25.07, 21.96 (C-3 and (CH$_2$)$_6$CH$_2$O), 13.85 (CH$_3$) ppm. Anal. (C$_{13}$H$_{30}$N$_4$O$_3$Cl$_2$ 0.95 H$_2$O. 0.04 C$_8$H$_{17}$OH) C, H, N, Cl.

Synthesis of Analogs of Canavanine

Scheme 1: Synthesis of D-2-amino-3-(guanidinooxy) propionic acid (D-GOA)

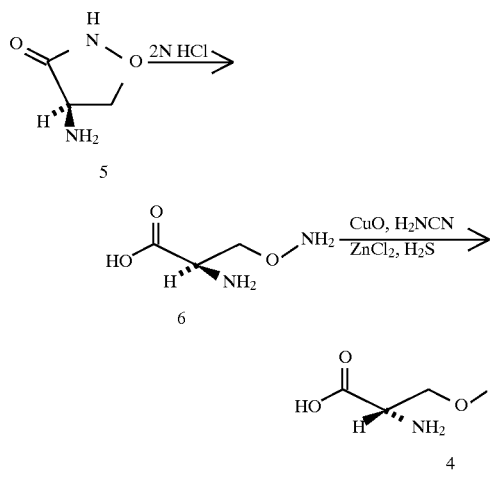

Scheme 2: Synthesis of L-2-amino-4-(1-imidazolidene-aminooxy) butanoic acid (L-ETCAV) and L-2-amino-4-[assym-N$^G$, N$^G$-dimethyl (guanidinooxy)]butanoic acid (L-DMCAV)

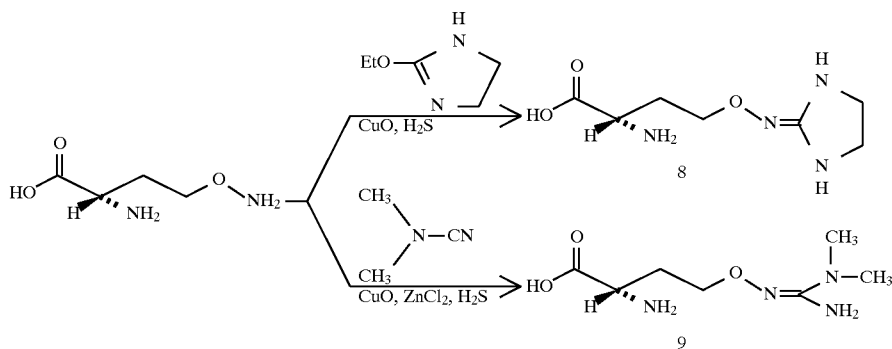

1) Synthesis of N,N'-ethylene canavanine

A)

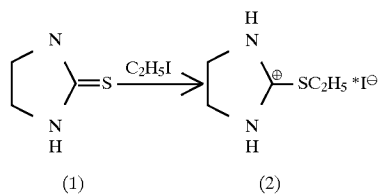

10.5 (0.10 mol) of N,N'-ethylenethiourea (98%) was suspended in 50 ml of EtOH (abs.). EtI (16.7 g, 0.11 mol) was added into this suspended solution. The reaction mixture was refluxed for 2 hours. After cooling the solution to RT, 50 ml of ethyl ether was added and the mixture was cooled to 40° C. and stayed for 3 hours at 4° C. The mixture was filtered and the solid was washed with ethyl ether. Yield 21.2 g (82.5%) of (2).

B)

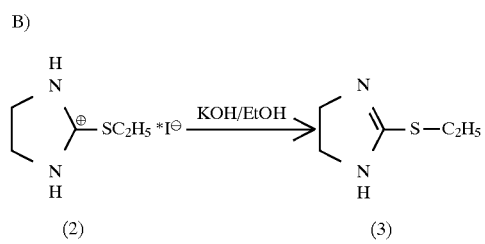

5.0 g (0.085 mol) of KOH was dissolved in 20 ml of EtOH (abs.) and 21.2 g (0.084 mol) of (2) was added into this solution. The mixture was stirred for 30 min. at RT, and 100 ml of water was added. The mixture was extracted with DCM (3×100 ml). The combined DCM solution was washed with water (3×200 ml) and dried over Na$_2$SO$_4$. Solvent was evaporated, to yield an oily residue of (3).

C)

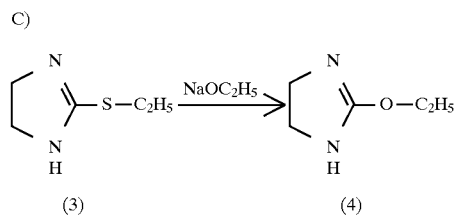

6.9 g (0.3 mol) of Na (metal) was dissolved in 100 ml of EtOH (abs.) and the solution was cooled to RT. Then the above oily residue of (3) was added into the ethyl alcohol solution and the mixture was refluxed for 72 hours. The solution was cooled to RT and 100 ml of water was added. The mixture was extracted with DCM (3×100 ml.), dried over $Na_2SO_4$. The solvent was evaporated. The yield of (4) was 6.79 g (71.4%).

D)

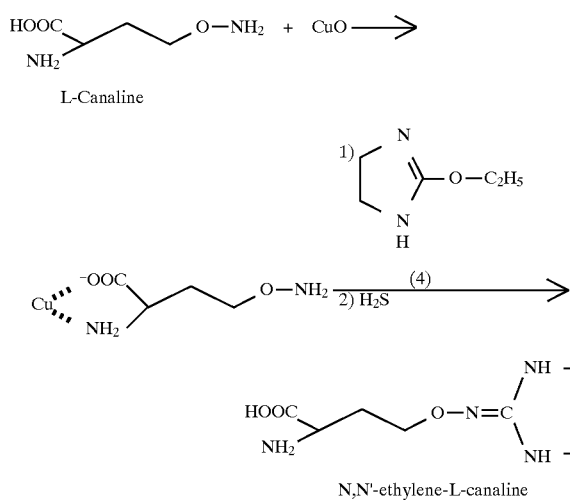

N,N'-ethylene-L-canaline 536 mg (4 mmol) of canaline was dissolved in 7 ml of water, and 954 mg (12 mmol) of CuO was added. The suspended solution was boiled for 5 min, then stirred for 2 hours at 50° C. and for 20 hours at RT. The excess CuO was removed by filtration. The pH of the solution was adjusted to 9.2 with 1N NaOH. 1.04 g (8 mmol) of (4) was added. The mixture was stirred for 90 hours at 45° C. Then $H_2S$ was bubbled into the mixture for 10 min. The CuS was removed by filtration. The solution was evaporated. The residue was dissolved in 1 ml of water. The products were precipitated from the solution using a mixture of ethanol and diethyl ether (1:1). The solid was purified by crystallization from ethanol (yield 32.3%).

2) Synthesis of N,N-dimethyl canavanine

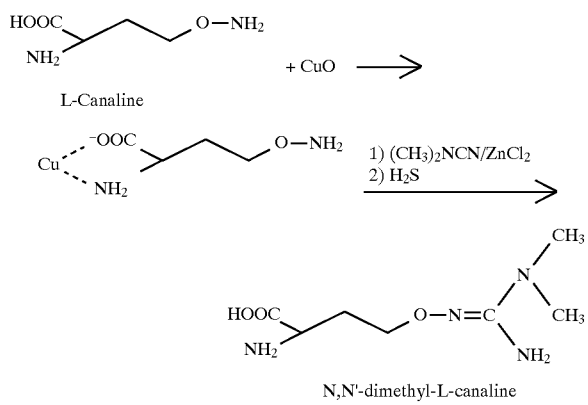

N,N'-dimethyl-L-canaline 536 mg (4 mmol) of canaline was dissolved in 3 ml of water, and 954 mg (12 mmol) of CuO was added. The suspended solution was boiled for 5 min. and stirred for two hours at 50° C. and 20 hours at RT. The excess CuO was removed by filtration. The pH of the solution was adjusted to 9.2. $ZnCl_2$(0.586 g, 4.31 mmol) and $(CH_3)_2NCN$ (0.302 g, 4.31 mmol) was dissolved in 4 ml of water, and the solution was added to the reaction mixture. The mixture was stirred for 72 h. at 45° C. Then $H_2S$ was bubbled into the solution for 20 min. The mixture was filtered and evaporated. The residue was purified by Dowex 50×8 ($NH_4^+$). The product was crystallized from ethanol (yield 30.3%).

3) Preparation of

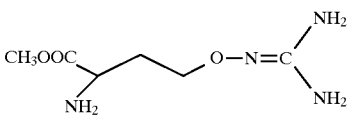

200 mg of dry L-canavanine was dissolved in 50 ml of MeOH (abs.). Anhydrous HCl was introduced into the solution for 10 min. Then the solution was refluxed for 1 h. with bubbling of HCl (20 bubble per min.). The solvent was then evaporated. The residue was recrystallized from methyl alcohol and diethyl ether, dried under vacuum, to yield 270 mg (90%) of the methyl ester. $^1$H-NMR ($D_2O$ +TSP), δ: 2.2–2.3 (2H. m); 3.72 (3H, s); 3.95–4.05 (2H, m); 4.15–4.22 (1H, m).

4) Preparation of

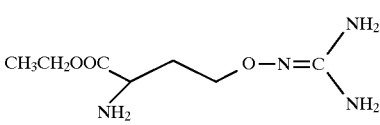

400 mg of dry L-canavanine was dissolved in 60 ml of EtOH (abs.). Anhydrous HCl was introduced into the solution for 10 min. Then the solution was refluxed for 2 h. with bubbling of HCl (20 bubble per min.). The solvent was then evaporated. The residue was recrystallized from methyl alcohol and diethyl ether, dried under vacuum, to yield 510 mg (81%). $^1$H-NMR (DMSO-$d_6$), δ: 1.19 (3H. t); 2.10–2.30 (2H, m); 3.85–3.95 (2H, m); 4.05–4.15 (1H, m); 4.17 (2H, q); 7.75–7.85 (5H, broad).

5) Preparation of

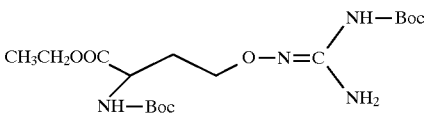

0.490 g (1.77 mmol) of ethyl-L-canavanine ester (2HCl salt) was dissolved in 5% $NaHCO_3$ (25 ml) and 25 ml of acetonitrile was added. 1.36 g (6 mmol) of di-t-butyl dicarbonate (97%) was added. The mixture was stirred for two days at RT. The acetonitrile was evaporated, and 20 ml of water was added. The aqueous solution was acidified by using 10 citric acid, and extracted with DCM (3×30 ml). The DCM solution was washed with water (4×30 ml), dried over $Na_2SO_4$ and evaporated. Yield of the N,N-diBOC derivative 0.57 g (79.3%). $^1$H-NMR ($CDCl_3$), δ: 1.22 (3H, t); 1.40 (9H, s); 1.42 (9H, s); 1.95–2.05 (1H, m); 2.05–2.15 (1H, m); 3.82–3.90 (2H, m); 4.15 (2H, q); 4.35–4.40 (1H, m); 5.35–5.40 [1H, d (broad)]; 5.97–6.03 (1H, broad).

6) Preparation of

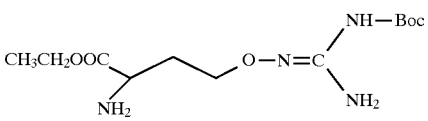

2.76 g (20 mmol) of sodium phosphate monobasic was dissolved in 20 ml of water (the concentration is 1M). The pH was adjusted to 7.8 with 2N NaOH. 0.277 g (1 mmol,) of ethyl-L-canavanine ester (2 HCl salt, MW: 277.11) was added into the buffer solution. Then 10 ml of ethyl alcohol was added together with 0.247 g (1.1 mol, MW 218) of t-butyl dicarbonate (97%). The solution was stirred for 20 hours at RT. Then the ethyl alcohol was evaporated and 20 ml of water was added. The aqueous solution was extracted with DCM (3×30 ml). The DCM solution was washed with water (3×20 ml), and dried over $Na_2SO_4$. The solvent was evaporated. Yield of the N-BOC derivative was 0.26 g (85%). $^1$H-NMR ($CDCl_3$), δ: 1.26 (3H, t); 1.42 (9H, s); 1.95–2.10 (1H, m); 2.10–2.05 (1H, m); 3.85–3.95 (2H, m); 4.19 (2H, q); 4.35–4.45 (1H, m); 5.30–5.40 (1H, broad).

7) Preparation of

8) Preparation of

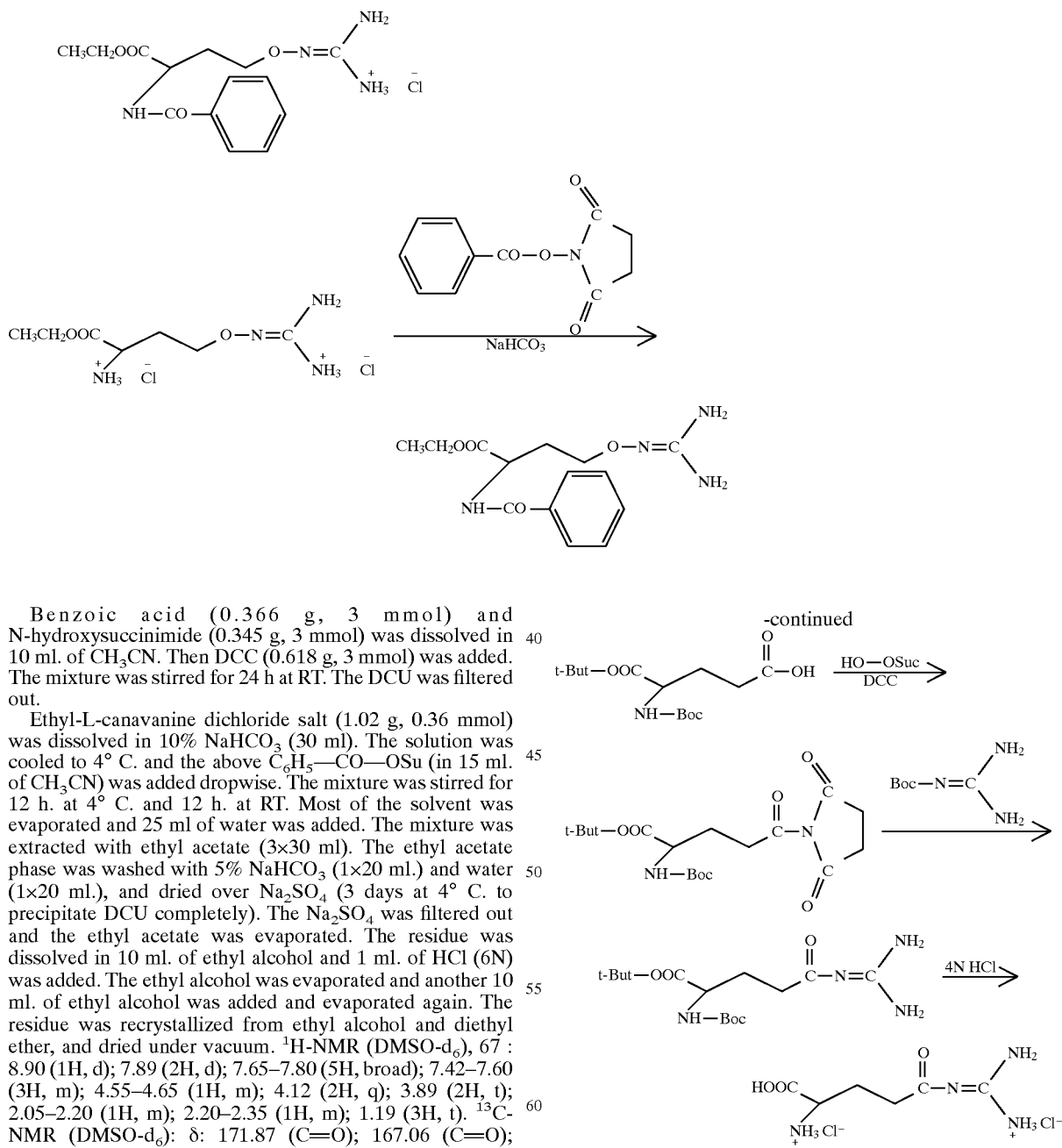

Benzoic acid (0.366 g, 3 mmol) and N-hydroxysuccinimide (0.345 g, 3 mmol) was dissolved in 10 ml. of $CH_3CN$. Then DCC (0.618 g, 3 mmol) was added. The mixture was stirred for 24 h at RT. The DCU was filtered out.

Ethyl-L-canavanine dichloride salt (1.02 g, 0.36 mmol) was dissolved in 10% $NaHCO_3$ (30 ml). The solution was cooled to 4° C. and the above $C_6H_5$—CO—OSu (in 15 ml. of $CH_3CN$) was added dropwise. The mixture was stirred for 12 h. at 4° C. and 12 h. at RT. Most of the solvent was evaporated and 25 ml of water was added. The mixture was extracted with ethyl acetate (3×30 ml). The ethyl acetate phase was washed with 5% $NaHCO_3$ (1×20 ml.) and water (1×20 ml.), and dried over $Na_2SO_4$ (3 days at 4° C. to precipitate DCU completely). The $Na_2SO_4$ was filtered out and the ethyl acetate was evaporated. The residue was dissolved in 10 ml. of ethyl alcohol and 1 ml. of HCl (6N) was added. The ethyl alcohol was evaporated and another 10 ml. of ethyl alcohol was added and evaporated again. The residue was recrystallized from ethyl alcohol and diethyl ether, and dried under vacuum. $^1$H-NMR (DMSO-$d_6$), 67 : 8.90 (1H, d); 7.89 (2H, d); 7.65–7.80 (5H, broad); 7.42–7.60 (3H, m); 4.55–4.65 (1H, m); 4.12 (2H, q); 3.89 (2H, t); 2.05–2.20 (1H, m); 2.20–2.35 (1H, m); 1.19 (3H, t). $^{13}$C-NMR (DMSO-$d_6$): δ: 171.87 (C=O); 167.06 (C=O); 158.36 (C=N); 133.67 (C—Ar); 131.90 (CH—Ar); 128.59 (CH—Ar); 127.60 (CH—Ar); 73.34 (O—$CH_2CH_3$); 61.02 (O—$CH_2CH_2$_); 49.70 (αCH); 28.88 (β-$CH_2$); 14.26 (CH_3). Calcd for $C_{14}H_{21}N_4O_4Cl$. ¼ $H_2O$: C:48.14; H: 6.18; N: 16.04; Cl: 10.16. Found: C: 48.20; H: 6.21; N: 15.54; Cl: 10.43.

NaOH (8.0 g, 0.2 mol) was dissolved in 400 ml. of a mixture of water and ethanol (1:1). After the solution was cooled to RT, guanidine hydrochloride (9.5 g, 0.1 mol) and di-t-butyl bicarbonate (Boc)$_2$O was added. The solution was stirred for 24 hours at RT. The ethanol was evaporated. The water solution was extracted with ethyl acetate (5×100 ml). The ethyl acetate solution was washed with water (2×20 ml), dried ($Na_2SO_4$) and the solvent removed to yield 3.1 g of N-t butyloxycarbonyl-guanidine [Boc—N=C($NH_2$)$_2$], 78.0%. $^1$H-NMR(CDCl$_3$): δ1.43 (9H, s); 6.10–6.20 (4H, broad). $^{13}$C-NMR (DMSO-d$_6$): δ: 163.216 (C=O); 162.68 (C=N); 75.56 [—O—C(CH$_3$)$_3$]; 28.23 (CH3).

Boc-Glu(OH)-t-butyl (0.606 g, 2.0 mmol) was dissolved in DCM (20 ml.). N-hydroxysuccinimide (HO—Suc) (0.253, 2.2 mmol) was added. The solution was cooled to 0° C. DCC (0.453 g, 2.2 mmol) was added. The solution was stirred for 2 hours at 0° C. and 20 hrs at RT. The DCU was filtered out. The solvent was evaporated. The residue was dissolved in 5 ml. of DCM and left to stand for 24 hours at 4° C. More DCU was filtered out. The solvent was evaporated again.

Boc—N=C(NH$_2$)$_2$ (0.477 g, 3 mmol) and TEA (0.648 g, 5 mmol) was dissolved in ethyl acetate (20 ml). The solution was cooled to 0° C. Boc-Glu(OSu)-t-But in 10 ml. of ethyl acetate was added. The mixture was stirred for 2 hours at 0° C. and 20 hours at RT. 20 ml of ethyl acetate was added and the solution was washed with 5% NaHCO$_3$ (2×30 ml.), water (1×30 ml), 5% citric acid (2×30 ml) and water (3×30 ml)m, dried over Na$_2$SO$_4$ and evaporated. The residue was recrystallized from ethyl acetate and hexanes. Yield 0.70 g, 78.8%. $^1$H-NMR(CDCl$_3$): δ1.44 (9H, s); 1.47(9H, s); 1.48 (9H, s); 1.86–2.00 (1H, m); 2.10–2.24 (1H, m);2.34–2.42 (2H, m); 4.16–4.25 (1H, m).

Ethyl acetate (20 ml) and 36% HCl (10 ml) was mixed and cooled to 0° C. Boc-Glu[N=C(NH$_2$)$_2$]-t-But (0.66 g, 1.48 mmol) was added. The solution was returned to RT and stirred for 1 h. at RT. The solvent was removed. 20 ml of ethyl alcohol was added and the solution evaporated and dried under vacuum. The residue was precipitated with ethyl alcohol and diethyl ether, and dried under vacuum. $^1$H-NMR (D$_2$O): δ: 2.17–2.27 (2H, m); 2.72–2.82 (2H, m); 3.93–4.00 (1H, m). $^{13}$C-NMR(D$_2$O): δ:177.90 (C=O); 175.50 (C=O); 157.30 (C=N); 55.66 (αCH); 35.27 (γ-CH$_2$); 27.13 (β-CH$_2$), Calcd for C$_6$H$_{14}$O$_3$N$_4$Cl$_2$O: C: 26.68; H: 5.60; N: 20.74; Cl: 26.25. Found: C: 26.71; H: 5.60; N: 20.77; Cl: 26.17.

9) Ethyl N$^α$-benzoyl-L-canavanine ester

Benzoic acid (0.366 g., 3 mmol) and N-hydroxysuccinimide (0.345 g, 3 mmol) was dissolved in 10 ml. of CH$_3$CN. DCC (0.618 g, 3 mmol) was then added. The mixture was stirred for 24 h. at RT. The DCU was filtered off.

Ethyl-L-canavanine ester dichloride salt (1.02 g, 0.36 mmol) was dissolved in 10% NaHCO$_3$ (30 ml). The solution was cooled to 4° C. and the above C$_6$H$_5$—CO—OSu (in 15 ml. of CH$_3$CN) was added dropwise. The mixture was stirred for 12 h. at 4° C. and 12 h. at RT. Most of the solvent was evaporated, and 25 ml of water was added. The mixture was extracted with ethyl acetate (3×30 ml). The ethyl acetate phase was washed with 5% NaHCO$_3$ (1×20 ml.) and water (1×20 ml.), and dried over Na$_2$SO$_4$ (3 days at 4° C. to precipitate the DCU completely). The Na$_2$SO$_4$ was filtered off and the ethyl acetate was evaporated. The residue was dissolved in 10 ml. of ethyl alcohol, and 1 ml. of HCl (6N) was added. The ethyl alcohol was evaporated and another 10 ml. of ethyl alcohol was added and the solution evaporated again. The residue was recrystallized from ethyl alcohol and diethyl ether, and dried under vacuum. $^1$H-NMR (DMSO-d$_6$), δ: 8.90 (1H, d); 7.89 (2H, d); 7.65–7.80 (5H, broad); 7.42–7.60 (3H, m); 4.55–4.65 (1H, m); 4.12 (2H, q); 3.89 (2H, t); 2.05–2.20 (1H, m); 2.20–2.35 (1H, m); 1.19 (3H, t).

$^{13}$C-NMR (DMSO-d$_6$): δ: 171.87 (C=O); 167.06 (C=O); 158.36 (C=N); 133.67 (C—Ar); 131.90 (CH—Ar); 128.59 (CH—Ar) 127.60 (CH—Ar); 73.34 (O—CH$_2$CH$_3$); 61.02 (O—CH$_2$CH$_2$—) 49.70 (α-CH); 28.88 (β-CH$_2$); 14.26 (CH$_3$). Calcd for C$_{14}$H$_{21}$N$_4$O$_4$Cl. ¼ H$_2$O: C: 48.14, H: 6.18; N: 16.04; Cl: 10.16. Found: C: 48.20; H: 6.21; N: 15.54; Cl: 10.43.

Further, the compounds of the present invention are useful in pharmaceutical compositions for systemic administration to humans and animals in unit dosage forms, such as tablets, capsules, pills, powders, granules, suppositories, sterile parenteral solutions or suspensions, sterile non-parenteral solutions or suspensions, oral solutions or suspensions, oil-in-water or water-in-oil emulsions and the like, containing suitable quantities of an active ingredient.

For oral administration either solid or fluid unit dosage forms can be prepared. The compounds are useful in pharmaceutical compositions (wt %) of the active ingredient with a carrier or vehicle in the composition of about 0.01 to 99% and preferably about 5 to 15%.

Either fluid or solid unit dosage forms can be readily prepared for oral administration. For example, the compounds can be mixed with conventional ingredients such as dicalciumphosphate, magnesium aluminum silicate, magnesium stearate, calcium sulfate, starch, talc, lactose, acacia, methyl cellulose and functionally similar materials such as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule.

Suspensions, syrups and elixirs may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives, produces an acceptable fluid preparation. A surfactant may be added to water to form a syrup for fluid unit dosages. Hydro-alcoholic pharmaceutical preparations may be used having an acceptable sweetener such as sugar, saccharine or a biological sweetener and a flavoring agent in the form of an elixir.

Pharmaceutical compositions for parenteral administration can also be obtained using techniques standard in the art as set forth in *Remington's Pharmaceutical Sciences,* 18th Ed., 1989, Mack Publishing Company, incorporated herein by reference it its entirety.

Accordingly, compositions suitable for administration are particularly included within the invention. Parenteral solutions or suspensions may be administered. If desired, a more concentrated slow release form may be administered. Accordingly, incorporation of the active compounds in a slow release matrix may be implemented for administering transdermally. The compounds may preferably be administered at about 1 to 20% of the composition and more preferably about 5 to 15% wt % of the active ingredient in the vehicle or carrier.

The above and other drugs can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving, stabilizing, wetting, emulsifying agents and the like together with the penetration enhancer of this invention.

The effective dosage for mammals may vary due to such factors as age, weight, activity level or condition of the subject being treated. Typically, an effective dosage of a compound according to the present invention is about 0.1 to 50 mg per kilogram of the subject's weight administered per day. Preferably about 25 to 50 mg per kilogram body weight is administered per day. The required dose is less when administered parenterally, preferably about 25–30 mg per kilogram of body weight per day may be administered intramuscularly.

REFERENCE

1. Douglass H. O., Tepper J., Leichman L. Neoplasms of the bile duct and pancreas, in: *Cancer Medicine,* Holland J. F., Frei et al. eds. Third edition: Lea and Febiger, 1993.
2. Cited in reference 1.
3. Cited in reference 1.
4. Wynder E. L. Cancer Res. 35:2228, 1975.
5. Kissane J. M., J Surg Oncol 7:167, 1975.
6. MacMahon B. Cancer 50:676, 1982.
7. Hermanck P. Eur J Surg Oncol 17:167, 1991.
8. Cited in reference 1.
9. Moosa A. R. Cancer 50:2689, 1982.
10. Apeiguist P. et al. J Surg Oncol 23:143, 1983.
11. Singh S. M. et al. Ann. Surg 212:132, 1990.
12. McGrath P. C. et al. Ann Surg 209:21, 1984.
14. Speer A. G. et al. Lancet 11:7, 1987.
15. Tepper J. et al. Cancer 37:1519, 1976.
16. Gastrointestinal tumor study group, Arch Surg 120:99, 1985.
17. Tepper J. E. In: *Cancer of the bile duct and pancreas,* Preeco P. E. et al. eds) W. B. Saunders Co., Philadelphia, 1989.
18. Sindelar W. F. & Kinsella T. J. Int J Radiat Oncol Biol Phys 12 (suppl 1): 48, 1986.
19. Abe M & Takahashi M. Int J Radiat Oncol Biol Phys 7:863, 1981.
20. Moertel C. G. et al. Surg 85:509, 1979.
21. Evans R. M. et al. Cancer Res 41:3288, 1981.
22. Keyomarski K. & Moran R. G. Cancer Res 46:5529, 1985.
23. Crown J et al. J Clin Oncol 9:1682, 1991.
24. Ardalan B & Singh G. J Clin Oncol 6:1053, 1988.
25. Nagourney R. A. et al. Proc Am Soc Clin Oncol 13:636, 1994.
26. Rosenthal G. A. *Plant Nonprotein Amino and Imino Acids, Biological, Biochemical, and Toxicological Properties*, Academic Press, San Diego, 1982.
27. Rosenthal G. A. Q Rev Biol 52, 155, 1977.
28. Rosenthal G. A. In: *Insecticides: Mechanism of Action and Resistance* D. Otto & B. Weber, eds. Intercept Ltd., Andover, England, 1982.
29. Rosenthal G. A. In: *Frontiers and New Horizons in Amino Acid Research,* K. Takai, ed. Elsevier, New York, 1992.
30. Rosenthal G. A. Phytochemistry 30:1055, 1991.
31. Rosenthal G. A. et al. J Biol Chem 264:13693, 1989.
32. Rosenthal G. A. et al. J Biol Chem 264:9768, 1989.
33. Rosenthal G. A. & Dahlman D. L. J Biol Chem 266:15684, 1991.
34. Thomas D. A. et al. Cancer Res 46:2898, 1986.
35. Rosenthal G. A. Unpublished experimental results.
36. Thomas D. A. & Rosenthal G. A. Toxicol & Appl Pharm 91:406, 1987.
(37) Rosenthal, G. A. Plant Nonprotein Amino and Imino Acids: Biological, Biochemical, and Toxicological Properties, Academic Press: San Diego, 1982; p. 273.
(38) Rosenthal, G. A. The Protective Action of a Higher Plant Toxic Product, BioScience, 1988, 38, 104–109.
(39) Rosenthal, G. A. L-Canavanine and Chemical Defense in Leguminous Plants. In Frontier and News Horizons in Amino Acid, Takai, K. Ed; Elsvier Science Publishing Co.: Amsterdam, 1992; pp. 109–118.
(40) Swaffar, D. S. et al., Inhibition of the Human Pancreatic Cancer Cells by the Arginine Antimetabolite L-Canavanine, Cancer Res. 1994, 54, 6045–6048.
(41) Swaffar, D. S.; Ang, C. Y., Desai, P. B.; Rosenthal, G. A.; Thomas D. A.; Crooks, P. A.; John, W. J. Combination Therapy with 5-Fluorouracil and L-Canavanine: In Vitro and In Vivo Studies, Anticancer Drugs, 1995, 6, 586–593.
(42) Rosenthal, G. A.; Dickey, K. M.; Gilding, H.: Crooks, P. A., Unpublished data.
(43) Boyar, A. and Marsh, R. E. L-Canavanine a Paradigm for the Structure of Substituted Guanidines. J. Am. Chem. Soc. 1982, 104, 1995–1998.
(44) Rosenthal, G. A. and Dahlman, D. L. Incorporation of L-Canavanine into proteins and the Expression of its Antimetabolic Effect. J. Agr. Food Chem. 1991, 39, 987–990.
(45) Rosenthal, G. A.; Dahlman, D. L.; Crooks, P. A.; Na Phuket, S.R.; Trifonov, L. S. Insecticidal Properties of Some Derivatives of L-Canavanine. J.Agr. Food Chem. 1995, 43 2728–2734.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. Canavanine analog compound having a formula selected from the group consisting of: Formula 1

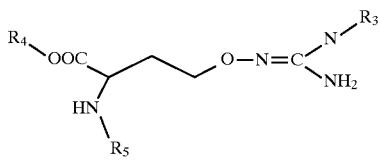

wherein $R_3$ is $H_2$; —$(CH_3)_2$; or H-Boc $R_4$ is —$CH_2CH_3$; or —$CH_3$ $R_5$ is H; H-Boc; or and

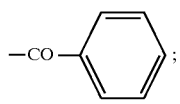

2. A canavanine analog compound of claim 1 wherein said compound is selected from the group consisting of
D-2-Amino-3-(aminooxy)propionic acid dihydrochloride;
D-2-Amino-3-(guanidinooxy)propionic acid;
L-2-Amino-4- [assym-$N^G$, $N^G$-dimethyl (guanidinooxy)] butanoic acid;
L-Canavanine Esters;
Methyl L-2-amino-4-guanidinooxybutanoate;
Ethyl L-2-amino-4-guanidinooxybutanoate;
Isopropyl L-2-amino-4-guanidinooxybutanoate;
n-Propyl L-2-amino-4-guanidinooxybutanoate;
n-Butyl L-2-amino-4-guanidinooxybutanoate;
n-Octyl-4-guanidinooxybutanoate, and mixtures thereof.

3. A canavanine analog compound of claim 2, wherein said L-Canavanine Esters are selected from the group consisting of methyl, ethyl, isopropyl and n-propyl esters of L-canavanine.

4. A pharmaceutical composition comprising a pharmaceutically effective amount of a compound according to claim 1 and a pharmaceutically acceptable carrier.

5. A pharmaceutical composition according to claim 4 wherein said compound is selected from the group consisting of
D-2-Amino-3-(aminooxy)propionic acid dihydrochloride;
D-2-Amino-3-(guanidinooxy)propionic acid;
L-2-Amino-4- [assym-$N^G$, $N^G$-dimethyl (guanidinooxy)] butanoic acid;
L-Canavanine Esters;
Methyl L-2-amino-4-guanidinooxybutanoate;
Ethyl L-2-amino-4-guanidinooxybutanoate;
Isopropyl L-2-amino-4-guanidinooxybutanoate;
n-Propyl L-2-amino-4-guanidinooxybutanoate;
n-Butyl L-2-amino-4-guanidinooxybutanoate;
n-Octyl-4-guanidinooxybutanoate and mixtures thereof.

6. A pharmaceutical composition according to claim 4 wherein said composition further comprises 5-fluorouracil.

7. A pharmaceutical composition according to claim 4 wherein said composition further comprises a compound selected from the group consisting of (S) -2-aminoethyl-L-cysteine, L-2-azetidine carboxylic acid, L-selenomethionine, L-3-[N-hydroxy-4-oxypyridyl]-2-aminopropionic acid and mixtures thereof.

8. A method of treating cancerous tumor comprising the steps of administering a pharmaceutically effective amount of a compound according to claim 1 to a patient with cancer.

9. A method of claim 8, wherein said cancer is pancreatic cancer.

10. A method of treating pancreatic cancer according to claim 1 wherein said compound is selected from the group consisting of
D-2-Amino-3-(aminooxy)propionic acid dihydrochloride;
D-2-Amino-3-(guanidinooxy)propionic acid;
L-2-Amino-4- [assym-$N^G$, $N^G$-dimethyl (guanidinooxy)] butanoic acid;
L-Canavanine Esters;
Methyl L-2-amino-4-guanidinooxybutanoate;
Ethyl L-2-amino-4-guanidinooxybutanoate;
Isopropyl L-2-amino-4-guanidinooxybutanoate;
n-Propyl L-2-amino-4-guanidinooxybutanoate;
n-Butyl L-2-amino-4-guanidinooxybutanoate;
n-Octyl-4-guanidinooxybutanoate and mixtures thereof.

11. A method of treating pancreatic cancer according to claim 10 wherein said composition further comprises 5-fluorouracil.

12. A method of treating pancreatic cancer according to claim 10, wherein said composition further comprises a compound selected from the group consisting of (S)-2-aminoethyl-L-cysteine, L-2-azetidine carboxylic acid, L-selenomethionine, L-3-[N-hydroxy-4-oxypyridyl]-2-amino-propionic acid and mixtures thereof.

13. A method of treating pancreatic cancer according to claim 10, wherein said pharmaceutically effective amount is about 25 to 50 mg per kilogram body weight a day.

14. Canavanine analog compound having a formula

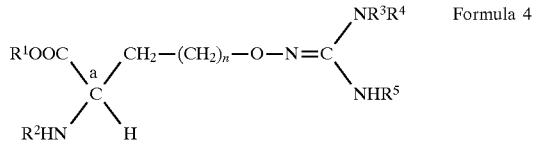

Formula 4 wherein
(a) $R^1$–$R^5$=H; n=0; a=S configuration
(b) $R^1$–$R^5$=H; n=1; a=S configuration
(c) $R^1$–$R^5$=H; n=1; a=R configuration
(d) $R^1$–$R^5$=H; n=2; a=S configuration
(e) $R^1$=$CH_3$; $R^2$–$R^5$=H; n=1; a=S configuration
(f) $R^1$=$CH_2CH_3$; $R^2$–$R^5$=H; n=1; a=S configuration
(g) $R^1$=$CH_2CH_2CH_3$; $R^2$–$R^5$=H; n=1; a=S configuration
(h) $R^1$=$CH(CH_3)_2$; $R^2$–$R^5$=H; n=1; a=S configuration
(i) $R^1$=$(CH_2)_3CH_3$; $R^2$–$R^5$=H; n=1; a=S configuration
(j) $R^1$=$(CH_2)_7CH_3$; $R^2$–$R^5$=H; n=1; a=S configuration
(k) $R^1R^3$=H; $R^4$, $R^5$=—$CH_2$—$CH_2$—, n=1; a=S configuration
(l) $R^1$=$R^2$=$R^5$=H; $R^3$=$R^4$=$CH_3$; n=1; a=S configuration
(m) $R^1$=$R^3$=$R^4$=$R^5$=H; $R^2$=$C_6H_5CO$; n=1; a=S configuration
(n) $R^1$=$CH_2$—$CH_3$; $R^2$=$C_6H_5CO$: $R^3$–$R^5$=H; n=1; a=S configuration.

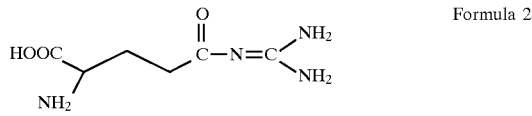

Formula 2

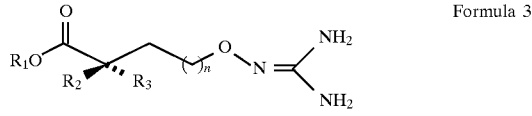

Formula 3

1 $R_1$=H, $R_2$=H, $R_3$=$NH_2$, n=1
2 $R_1$=H, $R_2$=H, $R_3$=$NH_2$, n=2
3 $R_1$=H, $R_2$=$NH_2$ $R_3$=H, n=1
10 $R_1$=methyl, $R_2$=H, $R_3$=$NH_2$, n=1
11 $R_1$=ethyl, $R_2$=H, $R_3$=$NH_2$, n=1
12 $R_1$=isopropyl, $R_2$=H, $R_3$=$NH_2$, n=1

13 R₁=n-propyl, R₂=H, R₃=NH₂, n=1
14 R₁=n-butyl, R₂=H, R₃=NH₂, n=1
15 R₁=n-octly, R₂=H, R₃=NH₂, n=1; and

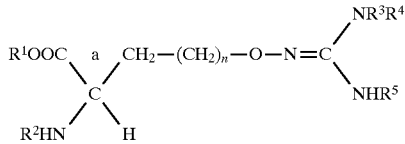

Formula 4

(a) $R^1$–$R^5$=H; n=0; a=S configuration
(b) $R^1$–$R^5$=H; n=1; a=S configuration
(c) $R^1$–$R^5$=H; n=1; a=R configuration
(d) $R^1$–$R^5$=H; n=2; a=S configuration
(e) $R^1$=CH₃; $R^2$–$R^5$=H; n=1; a=S configuration
(f) $R^1$=CH₂CH₃; $R^2$–$R^5$=H; n=1; a=S configuration
(g) $R^1$=CH₂CH₂CH₃; $R^2$–$R^5$=H; n=1; a=S configuration
(h) $R^1$=CH(CH₃)₂; $R^2$–$R^5$=H; n=1; a=S configuration
(i) $R^1$=(CH₂)₃CH₃; $R^2$–$R^5$=H; n=1; a=S configuration
(j) $R^1$=(CH₂)₇CH₃; $R^2$–$R^5$=H; n=1; a=S configuration
(k) $R^1$–$R^3$=H; $R^4$, $R^5$=—CH₂—CH₂—, n=1; a=S configuration
(l) $R^1$=$R^2$=$R^5$=H; $R^3$=$R^4$=CH₃; n=1; a=S configuration
(m) $R^1$=$R^3$=$R^4$=$R^5$=H; $R^2$=C₆H₅CO; n=1; a=S configuration
(n) $R^1$=CH₂—CH₃; $R^2$=C₆H₅CO; $R^3$–$R^5$=H; n=1; a=S configuration.

* * * * *